US010081614B2

(12) United States Patent
Söderman et al.

(10) Patent No.: US 10,081,614 B2
(45) Date of Patent: Sep. 25, 2018

(54) BIS(SULFONAMIDE) DERIVATIVES AND THEIR USE AS MPGES INHIBITORS

(71) Applicant: Acturum Real Estate AB, Solna (SE)

(72) Inventors: Peter Söderman, Stockholm (SE); Mats A. Svensson, Portland, OR (US); Annika Kers, Stockholm (SE); Liselott Öhberg, Järfälla (SE); Katharina Högdin, Knivsta (SE); Andreas Hettman, Trosa (SE); Jesper Hallberg, Stockholm (SE); Maria Ek, Solna (SE); Johan Bylund, Therwil (CH); Johan Nord, Västerås (SE)

(73) Assignee: ACTURUM REAL ESTATE AB, Solna (SE)

( * ) Notice: Subject to any disclaimer, the term of this patent is extended or adjusted under 35 U.S.C. 154(b) by 0 days.

(21) Appl. No.: 15/529,752

(22) PCT Filed: Nov. 24, 2015

(86) PCT No.: PCT/SE2015/051262
§ 371 (c)(1),
(2) Date: May 25, 2017

(87) PCT Pub. No.: WO2016/085392
PCT Pub. Date: Jun. 2, 2016

(65) Prior Publication Data
US 2017/0313672 A1 Nov. 2, 2017

(30) Foreign Application Priority Data

Nov. 27, 2014 (SE) ...................... 1451436

(51) Int. Cl.
*C07D 309/06* (2006.01)
*A61K 45/06* (2006.01)
*A61K 31/351* (2006.01)
*C07C 311/39* (2006.01)
*A61K 31/39* (2006.01)
*A61K 31/18* (2006.01)

(52) U.S. Cl.
CPC ............ *C07D 309/06* (2013.01); *A61K 31/18* (2013.01); *A61K 31/351* (2013.01); *A61K 45/06* (2013.01); *C07C 311/39* (2013.01)

(58) Field of Classification Search
CPC ... C07C 2601/14; C07C 311/39; A61K 45/06; A61K 31/18; A61K 31/351; C07D 309/06
USPC ........................................................ 549/426
See application file for complete search history.

(56) References Cited

U.S. PATENT DOCUMENTS

| 9,145,380 B2* | 9/2015 | Bylund | C07C 311/39 |
| 2005/0250818 A1* | 11/2005 | Koike | C07C 235/60 |
| | | | 514/350 |
| 2009/0131468 A1* | 5/2009 | Bylund | C07C 311/51 |
| | | | 514/302 |
| 2009/0163586 A1 | 6/2009 | Bylund et al. | |
| 2009/0281138 A1* | 11/2009 | Bylund | C07C 311/51 |
| | | | 514/302 |
| 2010/0292279 A1 | 11/2010 | Bylund et al. | |
| 2010/0331321 A1* | 12/2010 | Bylund | C07C 311/39 |
| | | | 514/230.5 |
| 2018/0002278 A1* | 1/2018 | Soderman | C07C 311/44 |

FOREIGN PATENT DOCUMENTS

| WO | WO 2007/042817 | 4/2007 |
| WO | WO 2008/129276 | 10/2008 |
| WO | WO 2008/129288 | 10/2008 |
| WO | WO 2009/064250 | 5/2009 |
| WO | WO 2009/064251 | 5/2009 |
| WO | WO 2009/082347 | 7/2009 |
| WO | WO 2010/132016 | 11/2010 |
| WO | WO 2016085391 | * 6/2016 |

OTHER PUBLICATIONS

Koeberle; Biochemical Pharmacology 2015, 98, 1-15. (Year: 2015).*
Beales et al., "Microsomal Prostaglandin E Synthas-1 inhibition blocks proliferation and enhances apoptosis in oesophageal adenocarcinoma cells without affecting endothelial prostacyclin production", Int. J. Cancer, 126, pp. 2247-2255, 2010.
Chaudhry et al., "Elevated Microsomal Prostaglandin-E Synthase-1 in Alzheimer's Disease", The Journal of the Alzheimer's Association, vol. 4, Issue 1, pp. 3-13, Jan. 2008.
Hernandez et al., "Overexpression of COX-2, Prostaglandin E Synthase-1 and Prostaglandin E Receptors in blood Mononuclear cells and plaque of patients with carotid atherosclerosis: Regulation by nuclear factor—kB", Atherosclerosis 187, pp. 139-149, 2006.
Hofstetter et al., "The Induced Prostaglandin E2 Pathway is a Key regulator of the Respiratory Response to Infection and Hypoxia in Neonates", PNAS, pp. 9894-9899, vol. 104, No. 23, Jun. 2007.
Isono et al., "Microsomal Prostaglandin E Synthase-1 Enhances Bone Cancer Growth and Bone Cancer-Related pain Behaviors in Mice", Life Sciences, 88, pp. 693-700, 2011.
Jakobsson et al., "Identification of Human Prostaglandin E Synthase: A Microsomal, Glutathione-dependent, Inducible enzyme, Constituting a Potential Novel Drug Target", Proc. Natl. Acad. Sci., vol. 96, pp. 7220-7225, Jun. 1999.
Jarowicki et al., Protecting Groups, J. Chem. Soc., Perkin Trans., 1, pp. 2109-2135, 2001.
Kamata et al., "mPGES-1-Expressing bone Marrow-derived cells enhance tumor growth and Angiogenesis in Mice", Biomedicine & Pharmacotherapy, 64, pp. 409-416, 2010.
Kojima et al., "Prostaglandin E Synthase in the Pathophysiology of Arthritis", Fundamental & Clinical Pharmacology, 19, pp. 255-261, 2005.

(Continued)

*Primary Examiner* — Daniel R Carcanague
(74) *Attorney, Agent, or Firm* — Baker & Hostetler LLP

(57) ABSTRACT

The present invention relates to bis(sulfonamide) compounds and pharmaceutically acceptable salts thereof. The present invention also relates to pharmaceutical compositions comprising these compounds and to their use as a medicament for the treatment and/or prevention of a disease, disorder or condition in which modulation of microsomal prostaglandin E synthase-1 activity is beneficial, such as pain, inflammation and cancer.

15 Claims, No Drawings

(56) References Cited

OTHER PUBLICATIONS

Kojima et al., Defective Generation of Humoral Immune Response Is Associate with a Reduced Incidence and Severity of Collagen-Induced Arthritis in Microsomal Prostaglandin E Synthase-1 Null Mice, J Immunol, 180(12), pp. 8361-8368, Jun. 2008.

Korotkova et al., "Effects of Immunosuppressive Treatment on Microsomal Prostaglandin E Synthase 1 and Cyclooxygenases Expression in Muscle Tissue of Patients with Polymyositis or Dermatomyositis", Ann Rheum Dis, 67(11), pp. 1596-1602, 2008.

Lu et al., "Microsomal Prostaglandin E Synthase-1 Promotes Hepatocarcinogenesis through Activation of a Novel EGR1 / β-Catenin Signaling Axis", Nature, 31, pp. 842-857, 2012.

Menter et al., "Prostaglandins in Cancer Cell Adhesion, Migration, and Invasion", Hindawi Publishing Corporation International Journal of Cell Biology, vol. 2012, 21 pages, 2012.

Nakanishi et al., "Genetic Deletion of mPGES-1 Suppresses Intestinal Tumorigenesis", Cancer Research, 68(9), May 2008.

Nakanishi et al., mPGES-1 as a Target for Cancer Suppression: a Compreshensive invited review "Phospholipase $A_2$ and Lipid Mediators", Biochimie, 92(6), pp. 660-664, Jun. 2010.

Patrignani et al., "Biochemical and Pharmacological Characterization of the Cyclooxygenase Activity of Human Blood Prostaglandin Endoperoxide Synthases", The Journal of Pharmacology and Experimental Therapeutics, vol. 271, No. 3, pp. 1705-1712, Aug. 1994.

Schroder et al., "15-deoxy-$^{12,14}$ prostaglandin $J^2$ Inhibits the Expression of Microsomal Prostaglandin E Synthase Type 2 in Colon Cancer Cells", Journal of Lipid Research, vol. 47, 2006.

Wang et al., "Clinical Implications of Microsomal Prostaglandin E Synthase-1 Overexpression in Human Non-Small-Cell Lung Cancer" Annals of Surgical Oncology, 13(9), pp. 1224-1234, Sep. 2006.

Wang et al., "Deletion of Microsomal Prostaglandin E Synthase-1 Augments Prostacyclin and Retards Atherogenesis" PNAS, vol. 103, No. 39, pp. 14507-14512, Sep. 2006.

Wang et al., "Microsomal Prostaglandin E Synthase-1 Deletion Suppresses Oxidative Stress and Angiotensin II-Induced Abdominal Aortic Aneurysm Formation" Vascular Medicine, 117(10), pp. 1302-1309, 2008.

Wang et al., Microsomal Prostaglandin E2 Synthase-1 Modulates the Response to Vascular Injury, Circulation, 123(6), pp. 631-639, 2011.

Xu et al., "MF63 [2-(6-Chloro-1H-Phenanthro[9,10-d]imidazole-2-yl)-isophthalonitrile], a selective Microsomal Prostaglandin E Synthase-1 Inhibitor, Relieves Pyresis and Pain in Preclinical Models of Inflammation", Journal of Pharmacology and Experimental Therapeutics, vol. 326, No. 3, May 2008.

* cited by examiner

BIS(SULFONAMIDE) DERIVATIVES AND THEIR USE AS MPGES INHIBITORS

CROSS-REFERENCE TO RELATED APPLICATIONS

This application is the National Stage of International Application No. PCT/EP2015/051262, filed Nov. 24, 2015, which claims the benefit of SE application number 1451436-8, filed Nov. 27, 2014, the disclosures of which are incorporated herein by reference in their entireties.

FIELD OF THE INVENTION

The present invention relates to bis(sulfonamide) compounds and pharmaceutically acceptable salts thereof. The present invention also relates to pharmaceutical compositions comprising these compounds, and to their use as medicaments for the treatment and/or prevention of a disease, disorder or condition in which modulation of microsomal prostaglandin E synthase-1 activity is beneficial, such as pain, inflammation and cancer.

BACKGROUND

Modulation of prostaglandin metabolism is at the centre of current anti-inflammatory therapies. NSAIDs and COX-2 inhibitors block the activity of cyclooxygenases and their ability to convert arachidonic acid into prostaglandin H2 (PGH2). PGH2 can be subsequently metabolized by terminal prostaglandin synthases to the corresponding biologically active PGs, namely, PGI2, thromboxane (Tx) A2, PGD2, PGF2α and PGE2. A combination of pharmacological, genetic and neutralizing antibody approaches demonstrates the importance of PGE2 in inflammation. The conversion of PGH2 to PGE2 by prostaglandin E synthases (PGES) may therefore represent a pivotal step in the propagation of inflammatory stimuli.

Microsomal prostaglandin E synthase-1 (mPGES-1) is an inducible PGES after exposure to pro-inflammatory stimuli. mPGES-1 is induced in the periphery and in the CNS by inflammation and represents therefore a target for acute and chronic inflammatory disorders.

PGE2 is a major prostanoid driving inflammatory processes. The prostanoid is produced from arachidonic acid liberated by Phospholipases (PLAs). Arachidonic acid is transformed by the action of Prostaglandin H Synthase (PGH Synthase, cyclooxygenase) into PGH2, which is a substrate for mPGES-1, which is the terminal enzyme transforming PGH2 to the pro-inflammatory PGE2.

NSAIDs reduce PGE2 by inhibiting cyclooxygenase, but at the same time reducing other prostanoids, giving side effects such as ulcerations in the GI tract. mPGES-1 inhibition gives a similar effect on PGE2 production without affecting the formation of other prostanoids, and hence a more favourable profile.

By blocking the formation of PGE2 in animal models of inflammatory pain a reduced inflammation, pain and fever response has been demonstrated (see e.g. Kojima et. al, *The Journal of Immunology* 2008, 180(12): 8361-8368; Xu et al., *The Journal of Pharmacology and Experimental Therapeutics* 2008, 326(3): 754-763).

Osteoarthritis is an inflammation of one or more joints, caused by the loss of cartilage leading to loss of water, while rheumatoid arthritis is considered to be of autoimmune origin. In several models of arthritis, inhibition of mPGES-1 leads to a reduced inflammation and/or pain (Kojima et al., *Fundamental & Clinical Pharmacology* 2005, 19(3): 255-261).

In abdominal aortic aneurism, inflammation leads to connective tissue degradation and smooth muscle apoptosis ultimately leading to aortic dilation and rupture. In animals lacking mPGES-1 a slower disease progression and disease severity has been demonstrated (see e.g. Wang et al., *Circulation* 2008, 117(10): 1302-1309).

Several lines of evidence indicate that PGE2 is involved in malignant growth. PGE2 facilitates tumor progression of many different types of cancers, by stimulation of cellular proliferation and angiogenesis and by modulation of immunosuppression (see e.g. Menter et al., *International Journal of Cell Biology* 2012; Nakanishi et al., *Biochimie* 2010, 92(6): 660-664; Kamata et al., *Biomedicine & Pharmacotherapy* 2010, 64(6): 409-416; Beales et al., *Int. J. Cancer* 2010, 126(9): 2247-2255). In support of a role for PGE2 in carcinogenesis, genetic deletion of mPGES-1 in mice suppresses the intestinal tumourogenesis (Nakanishi et al., *Cancer Research* 2008, 68(9): 3251-3259), hepatocarcinogenesis (Lu et al., *Oncogene* 2012, 31(7): 842-857) and bone cancer (Isono) et al., *Life Sciences* 2011, 88(15-16): 693-700). In man, mPGES-1 is also upregulated in cancers such as colorectal cancer (see e.g. Schröder et al., *Journal of Lipid Research* 2006, 47(5): 1071-80) and non-small-cell lung cancer (NSCLS) (Wang et al., *Annals of Surgical Oncology* 2006, 13(9): 1224-1234).

Myositis is chronic muscle disorder characterized by muscle weakness and fatigue. Proinflammatory cytokines and prostanoids have been implicated in the development of myositis. In skeletal muscle tissue from patients suffering from myositis, an increase in cyclooxygenases and mPGES-1 has been demonstrated, implicating mPGES-1 as a target for treating this condition (see e.g. Korotkova et al., *Annals of the Rheumatic Diseases* 2008, 67(11): 1596-1602).

In atherosclerosis, inflammation of the vasculature leads to atheroma formation that eventually may progress into infarction. In patients with carotid atherosclerosis, an increase in mPGES-1 in plaque regions has been found (Gómez-Hernández et al., *Atherosclerosis* 2006, 187(1): 139-149). In an animal model of atherosclerosis, mice lacking the mPGES-1 receptor were found to show a retarded atherogenesis and a concomitant reduction in macrophage-derived foam cells together with an increase in vascular smooth muscle cells (see e.g. Wang et al., *Proceedings of National Academy of Sciences* 2006, 103(39): 14507-14512) and reduced neointimal hyperplasia (Wang et al. *Circulation* 2011, 123(6): 631-639).

PGE-2, produced via mPGES-1, exerts a control of apnea frequency and mPGES-1 KO mice show reduced sensitivity to IL-1 induced anoxia (Hofstetter et al., *Proceedings of National Academy of Sciences* 2007, 104(23), 9894-9899).

Inflammation is part of the Alzheimer pathology, and mPGES-1 levels are higher in neuronal tissue from AD patients (Chaudhry et al., *Alzheimer's & Dementia* 2008, 4(1): 6-13).

Bis(sulfonamide) compounds which are useful for the treatment of pain and inflammatory diseases have been suggested in WO2007/042817, WO2008/129276, WO2008/129288, WO2009/064250, WO2009/064251, WO2009/082347 and WO2010/132016.

There is still a need for compounds that have an improved potency and improved selectivity to PGE2. There is a need for compounds having reduced side effect, such as gastrointestinal and renal toxicity.

SUMMARY OF THE INVENTION

The present invention is directed to a compound of formula (I), or a pharmaceutically acceptable salt thereof

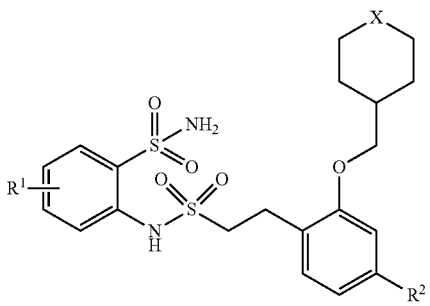

wherein:
$R^1$ is H or —CH$_2$OH;
$R^2$ is H, halogen, C$_{1-4}$-alkyl, fluoro-C$_{1-4}$-alkyl or —C≡C—R$^3$;
$R^3$ is H, C$_{1-4}$-alkyl, C$_{3-2}$-cycloalkyl or phenyl, wherein phenyl is optionally substituted with one or more substituents independently selected from C$_{1-4}$-alkyl, halogen, C$_{1-4}$-alkoxy and cyano;
X is CH$_2$, CHF, CF$_2$, O, S, SO, SO$_2$, NH or NR$^4$; and
$R^4$ is C$_{1-4}$alkyl.

The novel bis(sulfonamide) compounds are selective inhibitors of the microsomal prostaglandin E synthase-1 enzyme. The compounds are believed to have an improved potency and selectivity by selectively inhibiting the pro-inflammatory PGE2. It is believed that the compounds of the invention would have a reduced potential for side effects associated with the inhibition of other prostaglandins compared to conventional non-steroidal anti-inflammatory drugs. The compounds of the invention are believed to have a reduced gastrointestinal and renal toxicity.

Another embodiment relates to the compound of formula (I), wherein
$R^1$ is H or —CH$_2$OH;
$R^2$ is H, halogen, C$_{1-4}$-alkyl, fluoro-C$_{1-4}$-alkyl or —C≡C—R$^3$;
$R^3$ is C$_{1-4}$-alkyl, C$_{3-2}$-cycloalkyl or phenyl, wherein phenyl is optionally substituted with one or more C$_{1-4}$-alkyl;
X is CH$_2$, CHF, CF$_2$, O, S, SO, SO$_2$, NH or NR$^4$; and
$R^4$ is C$_{1-4}$alkyl.

A further embodiment relates to the compound of formula (I), wherein
$R^1$ is H or —CH$_2$OH;
$R^2$ is bromine, chlorine, fluorine, CH$_3$, CF$_3$ or —C≡C—R$^3$;
$R^3$ is C$_{1-4}$-alkyl, C$_{3-2}$-cycloalkyl or phenyl, wherein phenyl is optionally substituted with one or more C$_{1-4}$-alkyl; and
X is CH$_2$, CF$_2$ or O.

One embodiment relates to the compound of formula (I), wherein
$R^1$ is H or —CH$_2$OH;
$R^2$ is bromine, chlorine, fluorine, CH$_3$, CF$_3$ or —C≡C—R$^3$;
$R^3$ is C$_{1-4}$-alkyl, C$_{3-2}$-cycloalkyl or phenyl, wherein phenyl is optionally substituted with one or more C$_{1-4}$-alkyl; and
X is CF$_2$ or O.

Yet another embodiment relates to the compound of formula (I), wherein
$R^1$ is H or —CH$_2$OH;
$R^2$ is bromine, chlorine, fluorine, CH$_3$, CF$_3$ or —C≡C—R$^3$;
$R^3$ is tert-butyl, iso-propyl, cyclopropyl, cyclobutyl, cyclopentyl, phenyl, wherein phenyl is optionally substituted with a CH$_3$ group; and
X is CF$_2$ or O.

One embodiment relates to the compound of formula (I), wherein
$R^1$ is H or —CH$_2$OH;
$R^2$ is bromine, chlorine, fluorine, CH$_3$, CF$_3$ or —C≡C—R$^3$;
$R^3$ is tert-butyl, iso-propyl, cyclobutyl, cyclopropyl, cyclopentyl, phenyl, wherein phenyl is optionally substituted with a CH$_3$ group; and
X is O.

Yet another embodiment relates to the compound of formula (I), wherein
$R^1$ is H; $R^2$ is bromine, chlorine, fluorine, CH$_3$, CF$_3$ or —C≡C—R$^3$;
$R^3$ is tert-butyl, iso-propyl, cyclopropyl, cyclobutyl, cyclopentyl, phenyl, wherein phenyl is optionally substituted with a CH$_3$ group; and
X is O.

One embodiment relates to the compound of formula (I), wherein $R^1$ is H;
$R^2$ is bromine, chlorine, fluorine, CH$_3$, CF$_3$ or —C≡C—R$^3$;
$R^3$ is tert-butyl, iso-propyl, cyclopropyl, cyclobutyl, cyclopentyl, phenyl, wherein phenyl is optionally substituted with a CH$_3$ group; and
X is CF$_2$.

Yet another embodiment relates to the compound of formula (I), wherein
$R^1$ is —CH$_2$OH;
$R^2$ is bromine, chlorine, fluorine, CH$_3$, CF$_3$ or —C≡C—R$^3$;
$R^3$ is tert-butyl, iso-propyl, cyclobutyl, cyclopropyl, cyclopentyl, phenyl, wherein phenyl is optionally substituted with a CH$_3$ group; and
X is CF$_2$ or O.

Another embodiment relates to the compound of formula (I), wherein
$R^1$ is —CH$_2$OH;
$R^2$ is bromine, chlorine, fluorine, CH$_3$, CF$_3$ or —C≡C—R$^3$;
$R^3$ is tert-butyl, iso-propyl, cyclopropyl, cyclobutyl, cyclopentyl, phenyl, wherein phenyl is optionally substituted with a CH$_3$ group; and
X is O.

The selectivity and/or potency can be improved by compounds of formula (I), whereby the substituents on $R^1$ and X, are relatively short.

One embodiment relates to the compound of formula (I), wherein $R^1$ is —CH$_2$OH. Compounds of formula (I), whereby $R^1$ is —CH$_2$OH have good binding properties.

Another embodiment relates to the compound of formula (I), wherein $R^2$ is chlorine. Compounds of formula (I), whereby $R^2$ is chlorine have good binding properties.

A further embodiment relates to the compound of formula (I), wherein X is O. Compounds of formula (I), whereby X is O have good binding properties.

The invention also relates to any one of compounds, or a pharmaceutically acceptable salt thereof, selected from
2-[({2-[4-Bromo-2-(tetrahydro-2H-pyran-4-ylmethoxy)phenyl]ethyl}sulfonyl)amino]benzenesulfonamide,
2-[({2-[4-Chloro-2-(tetrahydro-2H-pyran-4-ylmethoxy)phenyl]ethyl}sulfonyl)amino]benzenesulfonamide,
2-[({2-[2-(Tetrahydro-2H-pyran-4-ylmethoxy)-4-(trifluoromethyl)phenyl]ethyl}sulfonyl)amino]benzenesulfonamide,
2-[({2-[4-methyl-2-(tetrahydro-2H-pyran-4-ylmethoxy)phenyl]ethyl}sulfonyl)amino]benzenesulfonamide, 2-[({2-[4-Fluoro-2-(tetrahydro-2H-pyran-4-ylmethoxy)phenyl]ethyl}sulfonyl)amino]benzenesulfonamide,
2-{[(2-{4-Chloro-2-[(4,4-difluorocyclohexyl)methoxy]phenyl}ethyl)sulfonyl]amino}benzenesulfonamide,
2-{[(2-{2-[(4,4-Difluorocyclohexyl)methoxy]-4-methylphenyl}ethyl)sulfonyl]amino}benzenesulfonamide,
2-{[(2-{2-[(4,4-Difluorocyclohexyl)methoxy]-4-fluorophenyl}ethyl)sulfonyl]amino}benzenesulfonamide,
2-[({2-[4-(Phenylethynyl)-2-(tetrahydro-2H-pyran-4-ylmethoxy)phenyl]ethyl}sulfonyl)amino]benzenesulfonamide,
2-[({2-[4-(Cyclopentylethynyl)-2-(tetrahydro-2H-pyran-4-ylmethoxy)phenyl]ethyl}sulfonyl)amino]benzenesulfonamide,
2-[({2-[4-(Cyclopropylethynyl)-2-(tetrahydro-2H-pyran-4-ylmethoxy)phenyl]ethyl}sulfonyl)amino]benzenesulfonamide,
2-[({2-[4-(cyclobutylethynyl)-2-(tetrahydro-2H-pyran-4-ylmethoxy)phenyl]ethyl}sulfonyl)amino]benzenesulfonamide,
2-[({2-[4-(3-methylbut-1-yn-1-yl)-2-(tetrahydro-2H-pyran-4-ylmethoxy)phenyl]ethyl}sulfonyl)amino]benzenesulfonamide,
2-{[(2-{4-[(4-Methylphenyl)ethynyl]-2-(tetrahydro-2H-pyran-4-ylmethoxy)phenyl}ethyl)sulfonyl]amino}benzenesulfonamide,
2-[({2-[4-(3,3-Dimethylbut-1-yn-1-yl)-2-(tetrahydro-2H-pyran-4-yl-methoxy)phenyl]ethyl}sulfonyl)amino]benzenesulfonamide,
2-[({2-[4-chloro-2-(tetrahydro-2H-pyran-4-ylmethoxy)phenyl]ethyl}sulfonyl)amino]-5-(hydroxymethyl)benzenesulfonamide, and
2-[({2-[4-fluoro-2-(tetrahydro-2H-pyran-4-ylmethoxy)phenyl]ethyl}sulfonyl)amino]-5-(hydroxymethyl)benzenesulfonamide.

These compounds fall within the scope of compounds of formula (I). It is to be understood that this list of compounds is included in the wording "compound of formula (I), or a pharmaceutically acceptable salt thereof", as used in embodiments related to uses, pharmaceutical compositions or processes, unless specified otherwise.

The invention also relates to the compound of formula (I), or a pharmaceutically acceptable salt thereof, as defined above, for use in therapy. In an embodiment, the invention relates to a compound of formula (I), or a pharmaceutically acceptable salt thereof, for use in the treatment or prevention of a disease, disorder or condition in which modulation of microsomal prostaglandin E synthase-1 activity is beneficial, such as pain, cancer, inflammation, apnea, sudden infant death (SID), atherosclerosis, aneurysm, hyperthermia, myositis, Alzheimer's disease, arthritis, osteoarthritis, rheumatoid arthritis, stroke or dementia. One embodiment relates to a use of the compound of formula (I), or a pharmaceutically acceptable salt thereof, as defined above, in therapy.

Another embodiment relates to the compound of formula (I), or a pharmaceutically acceptable salt thereof, as defined above, for use in prevention and/or treatment of pain.

A further embodiment relates to the compound of formula (I), or a pharmaceutically acceptable salt thereof, as defined above, for use in prevention and/or treatment of acute or chronic pain, nociceptive pain or neuropathic pain. Another embodiment relates to the compound of formula (I), or a pharmaceutically acceptable salt thereof, as defined above, for use in prevention and/or treatment of nociceptive pain. In one embodiment, the invention relates to a compound of formula (I), or a pharmaceutically acceptable salt thereof, for use in the treatment or prevention of inflammatory pain, headache and musculoskeletal pain.

One embodiment relates to the compound of formula (I), or a pharmaceutically acceptable salt thereof, as defined above, for use in prevention and/or treatment of cancer. Another embodiment relates to the compound of formula (I), or a pharmaceutically acceptable salt thereof, as defined above, for use in prevention and/or treatment of bone cancer, colorectal cancer, non-small-cell lung cancer or benign or malignant neoplasias.

Another embodiment relates to a use of the compound of formula (I), or a pharmaceutically acceptable salt thereof, as defined above, for use in the prevention and/or treatment of inflammation.

A further embodiment relates to the compound of formula (I), or a pharmaceutically acceptable salt thereof, as defined above, for use in the prevention and/or treatment of apnea, sudden infant death (SID), atherosclerosis, aneurysm, hyperthermia, myositis, Alzheimer's disease or arthritis.

Another embodiment relates to the compound of formula (I), or a pharmaceutically acceptable salt thereof, as defined above, for use in prevention and/or treatment of osteoarthritis or rheumatoid arthritis.

One embodiment relates to the compound of formula (I), or a pharmaceutically acceptable salt thereof, as defined above, for use in prevention and/or treatment of stroke or dementia.

The invention relates to a method of treating, preventing or reducing the risk of, a disease, disorder or condition in which modulation of microsomal prostaglandin E synthase-1 activity is beneficial, which comprises administering to a mammal, such as a human, in need thereof, a therapeutically effective amount of a compound of formula (I) as defined above or a pharmaceutically acceptable salt thereof.

The invention further relates to a pharmaceutical composition comprising the compound of formula (I), as defined above, or a pharmaceutically acceptable salt thereof, in the association with a pharmaceutically acceptable adjuvant, diluent or carrier.

The invention also relates to a process for the preparation of a pharmaceutical composition, as defined above, which comprises mixing a compound of formula (I), as defined above, or a pharmaceutically acceptable salt thereof, with a pharmaceutically acceptable adjuvant, diluent or carrier.

One embodiment relates to a use of the pharmaceutical composition, as defined above, in therapy, or for the prevention and/or treatment of a disease, disorder or condition in which modulation of microsomal prostaglandin E synthase-1 activity. Examples of such disease, disorder or condition are mentioned above.

The invention also relates to the use of a compound of formula (I), or a pharmaceutically acceptable salt thereof, as defined above, in the manufacture of a medicament for the treatment or prevention of a disease, disorder or condition in which modulation of microsomal prostaglandin E synthase-1 activity is beneficial. Examples of such disease, disorder or condition are mentioned above.

The treatment of microsomal prostaglandin E synthase-1 activity related pathology defined herein may be applied as a sole therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents, or atypical antipsychotic agents. Cognitive enhancing agents, memory enhancing agents and acetyl choline esterase inhibitors include onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX).

Such conjoint treatment may be achieved by way of the simultaneous, sequential or separate dosing of the individual components of the treatment. Such combination products employ the compounds, or pharmaceutically acceptable salts thereof, of the invention.

In one embodiment, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) a pharmaceutically acceptable excipient, carrier or diluent.

In another embodiment, the invention relates to a pharmaceutical composition comprising (i) a compound of formula (I), or a pharmaceutically acceptable salt thereof, (ii) at least one agent selected from the group consisting of acetyl cholinesterase inhibitors, anti-inflammatory agents, cognitive enhancing agents, memory enhancing agents, and atypical antipsychotic agents, and (iii) a pharmaceutically acceptable excipient, carrier or diluent.

In another embodiment, the invention relates to a pharmaceutical composition comprising (i) a compound of formula (I), or a pharmaceutically acceptable salt thereof, (ii) at least one agent selected from the group consisting of onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX), and (iii) a pharmaceutically acceptable excipient, carrier or diluent.

Additional conventional chemotherapy or therapy may include one or more of the following categories of agents:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine and venlafaxine.

(ii) atypical antipsychotics such as quetiapine.

(iii) antipsychotics such as amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine and ziprasidone.

(iv) anxiolytics such as alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam and zolazepam.

(v) anticonvulsants such as carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine and zonisamide.

(vi) Alzheimer's therapies such as donepezil, memantine, rivastigmine, galantamine and tacrine.

(vii) Parkinson's therapies such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase.

(viii) migraine therapies such as almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan and zomitriptan.

(ix) stroke therapies such as abciximab, activase, NXY-059, citicoline, crobenetine, desmoteplase, repinotan, clopidogrel, eptifibatide, minocycline and traxoprodil.

(x) urinary incontinence therapies such as darafenacin, falvoxate, oxybutynin, propiverine, robalzotan, solifenacin and tolterodine.

(xi) neuropathic pain therapies including for example lidocain and capsaicin, and anticonvulsants such as gabapentin and pregabalin, and antidepressants such as duloxetine, venlafaxine, amitriptyline and klomipramine.

(xii) nociceptive pain therapies such as paracetamol; NSAIDS such as diclofenac, loxoprofen, naproxen, ketoprofen, ibuprofen, nabumeton, meloxicam and piroxicam; coxibs such as celecoxib, etoricoxib, lumiracoxib, rofecoxib, valdecoxib and parecoxib; and opioids such as morphine, oxycodone, buprenorfin and tramadol.

(xiii) insomnia therapies such as agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon and zolpidem.

(xiv) mood stabilizers such as carbamazepine, divalproex, gabapentin, lamotrigine, lithium, olanzapine, quetiapine, valproate, valproic acid and verapamil.

Such combination products employ the compounds of this invention within the dosage range described herein and the other pharmaceutically active compound or compounds within approved dosage ranges and/or the dosage described in the publication reference.

DETAILED DESCRIPTION OF THE INVENTION

The definitions set forth in this application are intended to clarify terms used throughout this application. The term "herein" means the entire application.

As used herein, the term "$C_{1-4}$-alkyl", used alone or as a suffix or prefix, is intended to include both branched and straight chain saturated aliphatic hydrocarbon groups having from 1 to 4 carbon atoms. Examples of $C_{1-4}$-alkyl include methyl, ethyl, n-propyl, i-propyl, n-butyl, i-butyl, sec-butyl and tert-butyl.

As used herein, the term "$C_{1-4}$-alkoxy", used alone or as a suffix och prefix, refers to a $C_{1-4}$-alkyl radical, which is attached to the remainder of the molecule through an oxygen atom. Examples of $C_{1-4}$-alkoxy include methoxy, ethoxy, n-propoxy, i-propoxy, n-butoxy, i-butoxy, sec-butoxy and tert-butoxy.

As used herein, the term "fluoro-$C_{1-4}$-alkyl", used alone or as a suffix or prefix, is intended to include both branched and straight chain saturated aliphatic hydrocarbon groups, having at least one fluoro substituent and having from 1 to 4 carbon atoms. Examples of fluoro-$C_{1-4}$-alkyl include, but are not limited to, fluoromethyl, difluoromethyl, trifluoromethyl, 1-fluoroethyl, difluoroethyl, trifluoroethyl, fluoropropyl, difluoropropyl, trifluoropropyl, fluorobutyl, difluorobutyl and trifluorobutyl.

As used herein, the term "$C_{3-7}$-cycloalkyl", used alone or as suffix or prefix, denotes a cyclic saturated alkyl group having a ring size from 3 to 7 carbon atoms and includes cyclopropyl, cyclobutyl, cyclopentyl, cyclohexyl and cycloheptyl.

As used herein, the term "halogen" or "halo", used alone or as suffix or prefix, is intended to include bromine, chlorine, fluorine or iodine.

As used herein, the term "optional" or "optionally" means that the subsequently described event or circumstance may but need not occur, and that the description includes instances where the event or circumstance occurs and instances where it does not.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "protecting group" means temporary substituents protecting a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been extensively reviewed (see, e.g. Jarowicki, K.; Kocienski, P. Perkin Trans. 1, 2001, issue 18, p. 2109).

As used herein, "pharmaceutically acceptable salts" refer to forms of the disclosed compounds, wherein the parent compound is modified by making acid or base salts thereof. Examples of pharmaceutically acceptable salts include, but are not limited to, mineral or organic acid salts of basic residues such as amines; alkali or organic salts of acidic residues, such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

A variety of compounds in the present invention may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. All chiral, diastereomeric and racemic forms are intended, to be included in the scope of the invention, unless the specific stereochemistry or isomeric form is specifically indicated.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol.

As used herein, the phrase "compounds or pharmaceutically acceptable salts" include hydrates and solvates thereof.

Compounds and salts described in this specification may be isotopically-labelled compounds (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is used will depend on the specific application of that radio-labelled derivative. For example, for in vitro receptor labelling and competition assays, compounds that incorporate $^{3}H$ or $^{14}C$ are often useful. For radio-imaging applications $^{11}C$ or $^{18}F$ are often useful. In some embodiments, the radionuclide is $^{3}H$. In some embodiments, the radionuclide is $^{14}C$. In some embodiments, the radionuclide is $^{11}C$. And in some embodiments, the radionuclide is $^{18}F$.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The optimum dosage and frequency of administration will depend on the particular condition being treated and its severity; the age, sex, size and weight, diet, and general physical condition of the particular patient; other medication the patient may be taking; the route of administration; the formulation; and various other factors known to physicians and others skilled in the art.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

Preparation of Compounds

Compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3$^{rd}$ Edition, Wiley-Interscience, New York, 1999.

General Methods

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

Microwave heating was performed in a Biotage Creator, Initiator or Smith Synthesizer Single-mode microwave cavity producing continuous irradiation at 2450 MHz. It is understood that microwaves (MW) can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR

NMR spectra were recorded on a 400-600 MHz NMR spectrometer fitted with a probe of suitable configuration. Spectra were recorded at room temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, CD$_3$OD δ 3.30, acetone-$d_6$ 2.04 or CDCl$_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column. A linear gradient was applied using for example mobile phase A (10 mM NH$_4$OAc in 5% CH$_3$OH or 5% CH$_3$CN (aq.), or 0.1% NH$_3$ (aq.) or 0.1% formic acid (aq.)) and B (CH$_3$OH or CH$_3$CN). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation, a capillary column was used for example DB-5MS, (J&M Scientific). A linear temperature gradient was applied.

Preparative Chromatography:

Preparative chromatography was run on a Waters FractionLynx system with an Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M NH$_4$OAc in MilliQ water and 5% MeCN) in B (100% MeCN) or a gradient of A (95% 0.1 M NH$_4$OAc in MilliQ water and 5% MeOH), A (0.2% NH$_3$ in MilliQ water) or A (0.2% formic acid in MilliQ water) in B (100% MeOH) was applied for LC-separation at flow rate 20 ml/min.

Preparative chiral chromatography for separation of isomers was run on for example an LaPrep® system using the specified column and mobile phase system.

SFC Analyses:

Supercritical Fluid Chromatography (SFC) was performed on a straight phase column. An isocratic flow was applied using mobile phase A (CO$_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS):

For accurate mass measurements, HRMS was performed on a Waters Synapt-G2 mass spectrometer equipped with a LockSpray source and connected to an Acquity UPLC system with a PDA detector and an Acquity UPLC BEH C18 column. The measured mass confirmed the elemental composition within 3 ppm.

ABBREVIATIONS

ACN acetonitrile
aq aqueous
Atm atmospheric pressure
Boc t-butoxycarbonyl
Borax di-sodium tetraborate or sodium borate or sodium tetraborate
Cbz benzyloxycarbonyl
CDI 1,1'-carbonyldiimidazole
dba dibenzylideneacetone
DCM dichloromethane
DEA diethylamine
DIBAL-H diisobutylaluminium hydride
DIPEA diisopropylethylamine
DMAP 4-Dimethylaminopyridine
DME 1,2-dimethoxyethane
DMF N,N-dimethyl formamide
DMSO dimethyl sulfoxide dppf 1,1'-bis(diphenylphosphino)ferrocene
Et₂O diethyl ether
EtOAc ethyl acetate
EtOH ethanol
eq. or equiv. equivalent
h hour(s)
HPLC high performance liquid chromatography
IPA isopropanol
LCMS liquid chromatography mass spectrometry
LiHMDS lithium bis(trimethylsilyl)amide
MeOH methanol
min minute(s)
MS mass spectrometry
MW microwave(s)
NH₄OAc ammonium acetate
NMR nuclear magnetic resonance
OX oxidation
Psi pounds per square inch
quant. quantitative
RCM ring closing metathesis
r.t. room temperature, i.e. between 16 to 25° C. Celcius
sat. saturated
SFC supercritical fluid chromatography
TFA trifluoroacetic acid
THF tetrahydrofuran
TLC thin layer chromatography
TMEDA tetramethylethylenediamine
UPLC ultra performance liquid chromatography
2-Me THF 2-methyl tetrahydrofuran Naming Compounds:

Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acd-labs.com, or Lexichem, version 1.9, software from OpenEye.

General Methods

Scheme 1

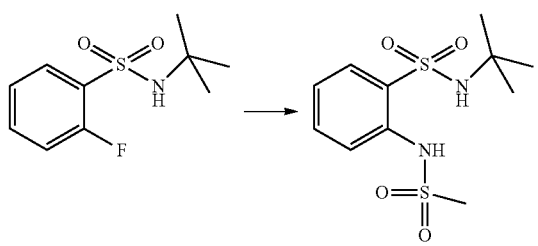

Scheme 2

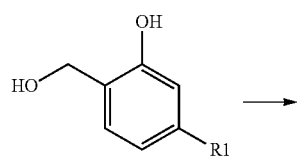

Scheme 3

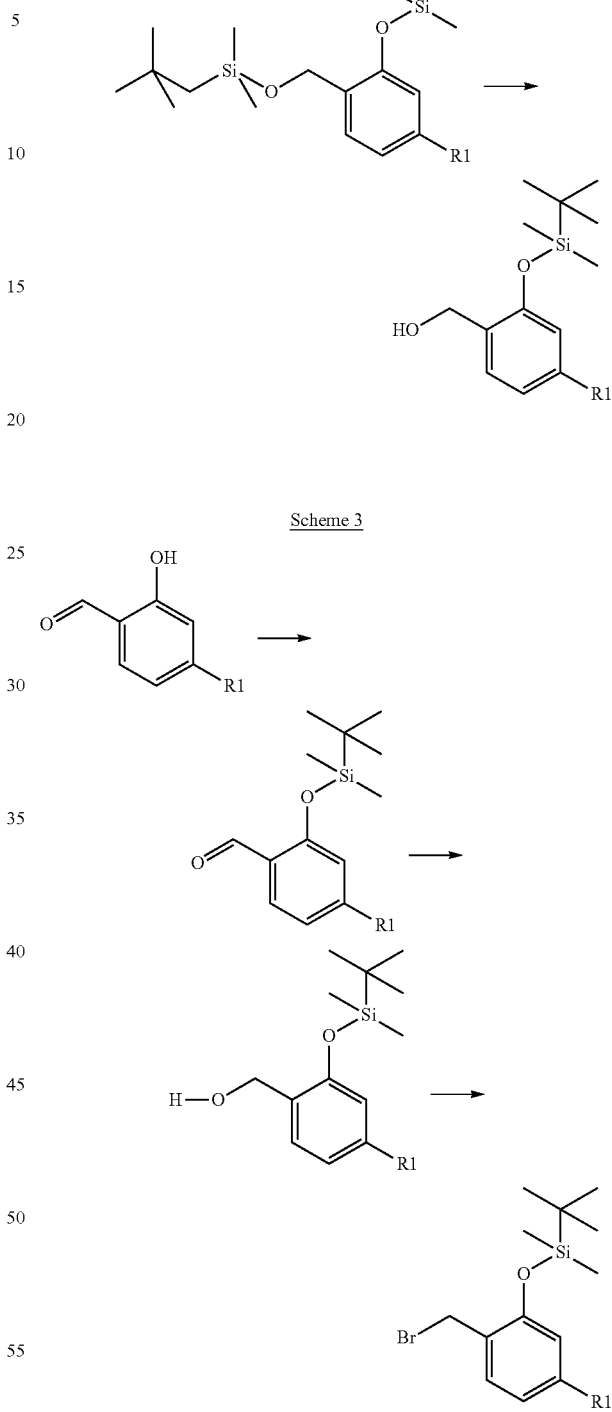

Scheme 4

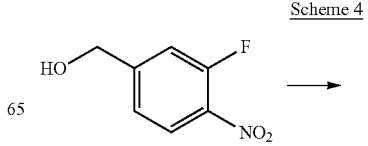

-continued
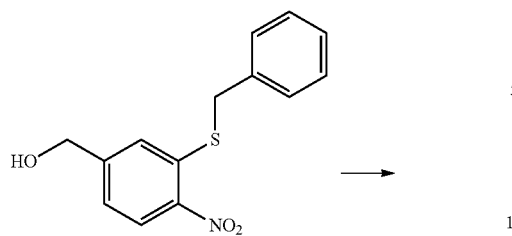
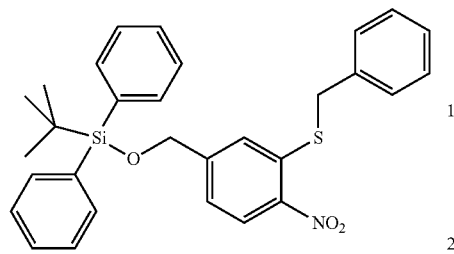
Scheme 5
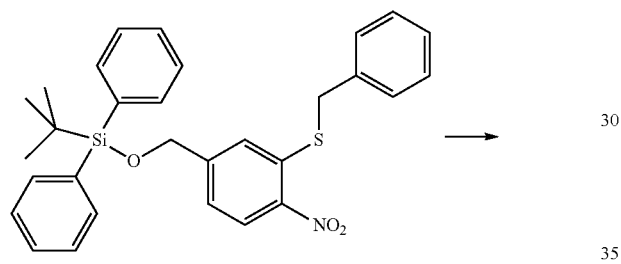
Scheme 6
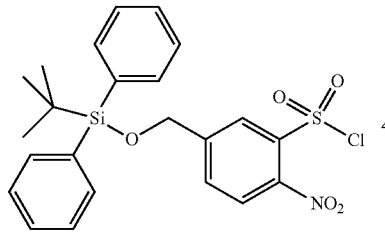
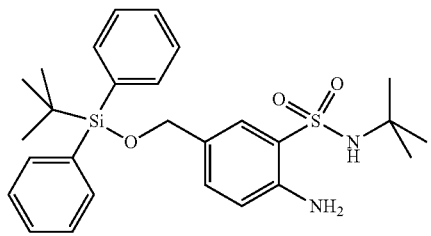
Scheme 7
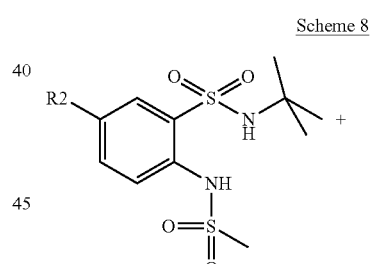
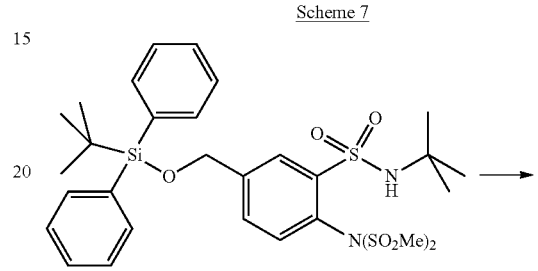
Scheme 8
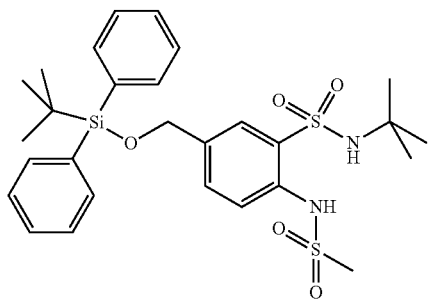
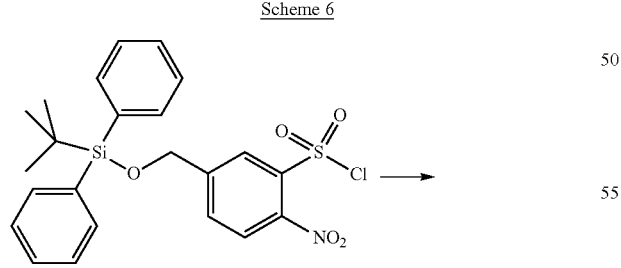
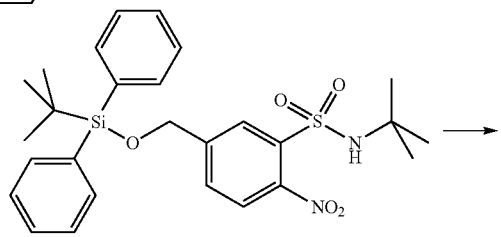
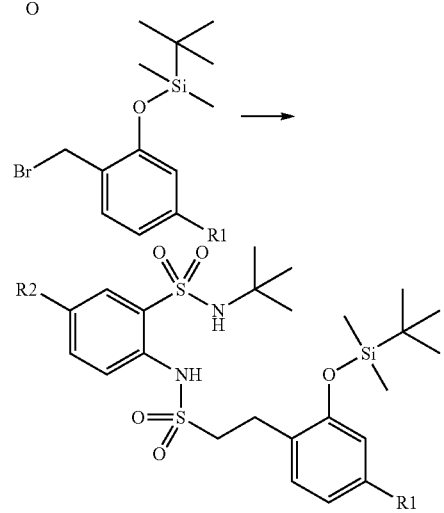

Scheme 9

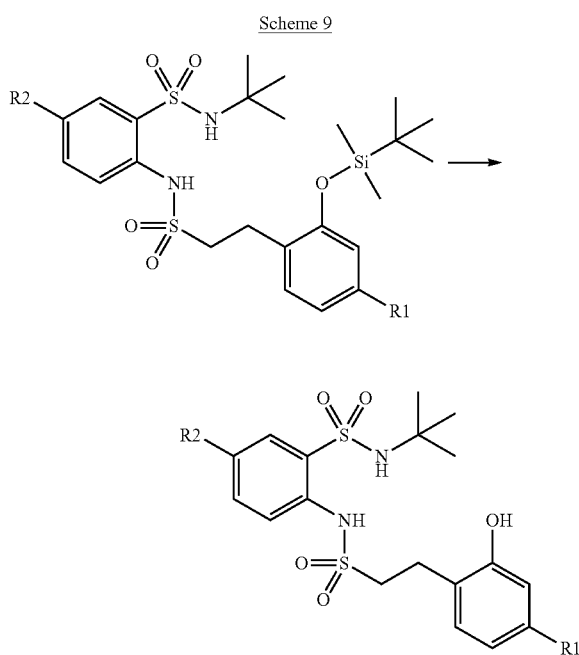

Scheme 10

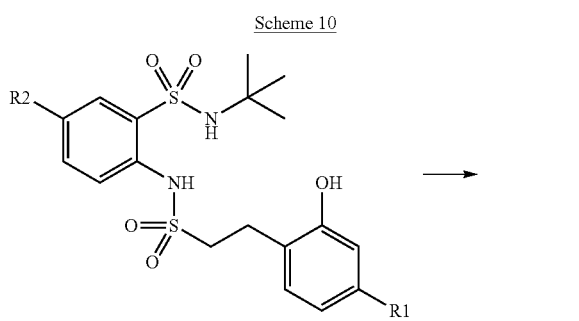

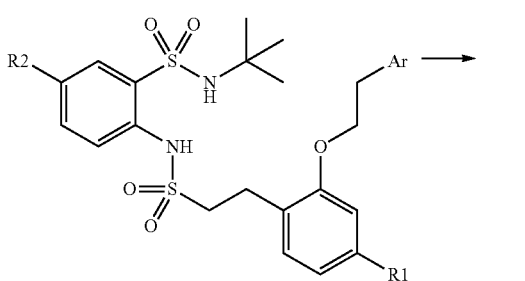

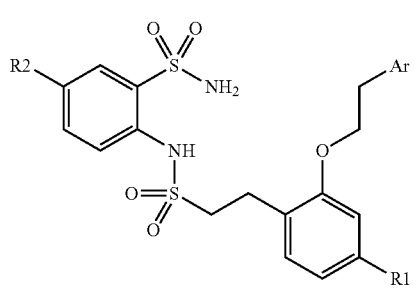

EXAMPLES

Below follows a number of non-limiting examples of compounds of the invention.

Intermediate 1

N-tert-Butyl-2-fluorobenzenesulfonamide

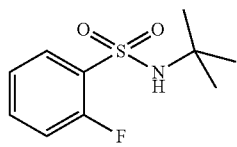

tert-Butylamine (0.99 mL, 9.42 mmol) was added dropwise to a cooled (0° C.) solution of 2-fluorobenzenesulfonyl chloride (0.50 mL, 3.78 mmol) in dichloromethane (5 mL) at room temperature for 1 h. Water and ethyl acetate was added and the aqueous phase was extracted with ethyl acetate. The combined organic phases were washed with water and brine, dried over sodium sulfate and the solvent was evaporated to yield 0.86 g (99% yield) of the title compound. $^1$H NMR (600 MHz, DMSO-$d_6$) δ ppm 7.79-7.85 (m, 1H) 7.75 (s, 1H) 7.64-7.70 (m, 1H) 7.38-7.44 (m, 1H) 7.33-7.38 (m, 1H) 1.11 (s, 9H); MS (ES$^-$) m/z 230 [M–H]$^-$.

Intermediate 2

N-tert-Butyl-2-[(methylsulfonyl)amino]benzenesulfonamide

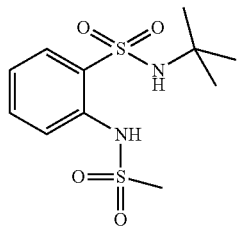 [SMILES: CC(C)(C)NS(=O)(=O)c1ccccc1NS(C)(=O)=O]

A mixture of N-tert-butyl-2-fluorobenzenesulfonamide (18 g, 78.01 mmol), methanesulfonamide (11.23 g, 118.10 mmol) and potassium carbonate (16.28 g, 117.80 mmol) in sulfolane (70 mL) was heated at 150° C. over 72 h.

Water was added and the resulting solid was removed by filtration. The aquepous phase was neutralized (pH~7.5) with aquepous hydrochloric acid (2 M) and extracted with ethyl acetate. The organic phase was washed with water, water/brine (1:1) and brine, dried over magnesium sulfate and the solvent was evaporated. Purification by chromatography on silica using gradient elution 60% EtOAc in heptane gave 17.22 g (72% yield of the title compound. $^1$H NMR (500 MHz, DMSO-$d_6$) δ ppm 1.11 (s, 9H) 3.17 (s, 3H) 7.32 (s, 1H) 7.60-7.71 (m, 2H) 7.89 (d, J=7.88 Hz, 1H) 8.01 (s, 1H) 8.72 (s, 1H); MS (ES$^-$) m/z 305 [M–H]$^-$.

Intermediate 3

4-Bromo-2-{[tert-butyl(dimethyl)silyl]oxy}benzaldehyde

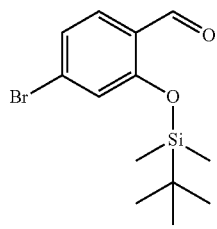 [SMILES: CC(C)(C)[Si](C)(C)Oc1cc(Br)ccc1C=O]

A solution of 4-bromo-2-hydroxybenzaldehyd (20.40 g, 101.49 mmol) and imidazole (6.99 g, 102.68 mmol) dissolved in anhydrous N,N-dimethylformamide (150 mL) was cooled to 0° C. t-Butyldimethylchlorosilane (18.57 mL, 102.24 mmol) was added and the reaction mixture was allowed to reach room temperature as the ice bath expired.

The reaction mixture was partioned between ethyl acetate and brine and the aqueous phase was extracted with ethyl acetate. The combined organic phases were washed with brine, dried over magnesium sulfate, filtered, and the solvent was evaporated. The product was kept under vacuum over night, which gave 32.7 g of the title compound, which was used without further purification in the next step. $^1$H NMR (500 MHz, DMSO-$d_6$) δ ppm 0.28-0.30 (m, 6H) 0.98 (s, 9H) 7.18-7.21 (m, 1H) 7.34 (dd, J=8.35, 1.42 Hz, 1H) 7.62 (d, J=8.20 Hz, 1H) 10.26 (s, 1H).

Intermediate 4

2-{[tert-Butyl(dimethyl)silyl]oxy}-4-chlorobenzaldehyde

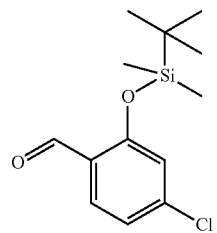 [SMILES: CC(C)(C)[Si](C)(C)Oc1cc(Cl)ccc1C=O]

The title compound was prepared following the procedure for Intermediate 3 starting from 4-chloro-2-hydroxybenzaldehyde (1.0 g, 6.39 mmol), imidazole (0.652 g, 9.58 mmol) and tert-butyldimethylchlorosilane (1.43 mL, 7.66 mmol) in DMF (15 mL). Stirring over 72 h at room temperature followed by concentration of the reaction mixture and purification by chromatography on silica using 25% EtOAc in heptane gave 1.1 g (64% yield) of the title compound. $^1$H NMR (500 MHz, CHLOROFORM-d) δ ppm 0.26-0.38 (m, 6H) 1.03 (s, 10H) 6.89 (d, 1H) 7.04 (dd, 1H) 7.76 (d, 1H) 10.39 (s, 1H).

Intermediate 5

2-{[tert-Butyl(dimethyl)silyl]oxy}-4-fluorobenzaldehyde

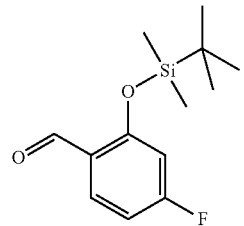 [SMILES: CC(C)(C)[Si](C)(C)Oc1cc(F)ccc1C=O]

The title compound was prepared following the procedure for Intermediate 3 starting from 4-fluoro-2-hydroxybenzaldehyde (5 g, 19.66 mmol), tert-butylchlorodimethylsilane (3.26 g, 21.62 mmol) and 1H-imidazole (3.35 g, 49.14 mmol) in acetonitrile (20 mL) and stirring at room temperature over night. The mixture was dissolved in water and made acidic using aqueous HCl (2 M) and extracted three times with EtOAc. The combined organic phases were washed with water, dried and concentrated under reduced pressure to give 3.77 g (58% yield) of the title compound. $^1$H NMR (500 MHz, CHLOROFORM-d) δ ppm 0.26-0.36 (m, 6H) 0.97-1.08 (m, 9H) 6.58 (dd, J=10.25, 2.36 Hz, 1H) 6.76 (d, J=2.21 Hz, 1H) 7.84 (dd, J=8.67, 7.09 Hz, 1H) 10.36 (s, 1H); MS (ES$^-$) m/z 331, 332, 333 [M−H]$^-$.

Intermediate 6

2-{[tert-Butyl(dimethyl)silyl]oxy}-4-methylbenzaldehyde

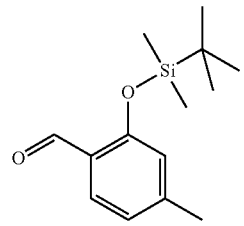 [SMILES: Cc1ccc(C=O)c(O[Si](C)(C)C(C)(C)C)c1]

The title compound was prepared following the procedure for Intermediate 3 starting from 2-hydroxy-4-methylbenzaldehyde (5.62 g, 41.26 mmol), imidazole (2.95 g, 43.37 mmol) and tert-butyldimethylchlorosilane (6.54 g, 43.39 mmol) in anhydrous N,N-dimethylformamide (40 mL). The reaction mixture was partioned between ethyl acetate and brine and the aqueous phase was extracted with ethyl acetate. The combined organic phases were washed with water and brine, dried over magnesium sulfate, filtered, and the solvent was removed under reduced pressure to give 10.10 g (98% yield) of the title compound that was used in the next step without further purification. $^1$H NMR (500 MHz, DMSO-$d_6$) δ ppm 0.24-0.30 (m, 6H) 0.95-1.02 (m, 9H) 2.34 (s, 3H) 6.82 (s, 1H) 6.93 (d, J=7.88 Hz, 1H) 7.58 (d, J=7.88 Hz, 1H) 10.27 (m, 1=0.60 Hz, 1H); MS (ES$^+$) m/z 251 [M+H]$^+$.

Intermediate 7

(4-Bromo-2-{[tert-butyl(dimethyl)silyl]oxy}phenyl)methanol

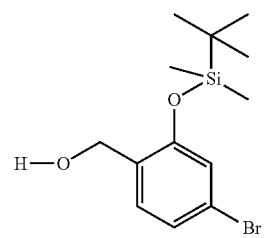 [SMILES: CC(C)(C)[Si](C)(C)Oc1cc(Br)ccc1CO]

To a cold 0° C. solution of 4-bromo-2-(tert-butyldimethylsilyloxy)benzaldehyde (6.05 g, 19.19 mmol) in methanol (50 mL) was sodium borohydride (1.09 g, 28.79 mmol) added portionwise. After addition was completed, the reaction was allowed to reach room temperature. After 2 h, the reaction was quenched with saturated ammonium chloride and the organic layer was washed with brine, and then dried over magnesium sulfate and concentrated. Purification by chromatography on silica using gradient elution 12.5% EtOAc in heptane gave 4.9 g (81% yield) of the title compound.

$^1$H NMR (500 MHz, CHLOROFORM-d) δ ppm 0.25-0.30 (m, 6H) 0.99-1.08 (m, 9H) 4.63 (d, 2H) 6.95 (d, 1H) 7.11 (dd, 1H) 7.21 (d, 1H); MS (ES$^+$) m/z 317, 318[M+H]$^+$.

Intermediate 8

(2-{[tert-Butyl(dimethyl)silyl]oxy}-4-chlorophenyl)methanol

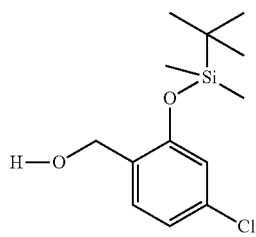 [SMILES: CC(C)(C)[Si](C)(C)Oc1cc(Cl)ccc1CO]

In a 500 mL round bottle flask was 2-{[tert-butyl(dimethyl)silyl]oxy}-4-chlorobenzaldehyde (26.5 g, 97.85 mmol) dissolved in anhydrous methanol (170 mL) and the solution was cooled to −20° C. with an acetone-dry ice bath. Sodium borohydride (4.44 g, 117.42 mmol) was added in small portions, keeping the temperature at −20. The mixture was stirred until it reached room temperature as the ice bath expired (2 h). The reaction was quenched by the addition of a solution of saturated ammonium chloride. The volume was reduced to ⅓ by evaporating the solvent. The reaction mixture was partioned between ethyl acetate and brine, and the aqueous layer was extracted once more with ethyl acetate. The combined organic extracts were washed with water, brine, dried over magnesium sulfate and the resulting liquid was dried at room temperature in vacuo to give 24.9 g (93% yield) of the title compound. $^1$H NMR (500 MHz, DMSO-d$_6$) δ ppm 0.22 (s, 6H) 0.97 (s, 9H) 4.45 (d, 2H) 5.13 (t, 1H) 6.78 (d, 1H) 7.03 (dd, 1H) 7.38 (d, 1H); MS (ES$^-$) m/z 271, 273, 275 [M−H]$^-$.

Intermediate 9

(2-{[tert-Butyl(dimethyl)silyl]oxy}-4-fluorophenyl)methanol

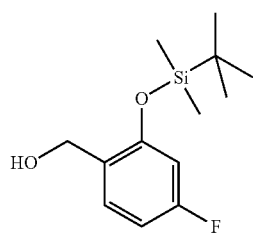 [SMILES: CC(C)(C)[Si](C)(C)Oc1cc(F)ccc1CO]

To a cold (0° C.) solution of 2-{[tert-butyl(dimethyl)silyl]oxy}-4-fluorobenzaldehyde (5.0 g, 19.66 mmol) in methanol (50 mL) sodium borohydride (1.12 g, 29.48 mmol) was added portionwise. After the addition was complete, the reaction was allowed to reach room temperature. After 2 h, the reaction was quenched with saturated ammonium chloride, the aqueous phase was washed with ethylacetate, and the organic layer was washed with brine, then dried over magnesium sulfate and concentrated. Purification by chromatography on silica using gradient elution 0-100% EtOAc in heptane gave 3.12 g (62% yield) of the title compound. $^1$H NMR (500 MHz, DMSO-d$_6$) δ ppm 0.20-0.24 (m, 6H) 0.95-1.01 (m, 9H) 4.44 (d, J=5.36 Hz, 2H) 6.59 (dd, J=10.40, 2.52 Hz, 1H) 6.79 (td, J=8.67, 2.52 Hz, 1H) 7.37 (dd, J=8.20, 7.57 Hz, 1H); MS (ES$^-$) m/z 255 [M−H]$^-$.

Intermediate 10

(2-{[tert-Butyl(dimethyl)silyl]oxy}-4-methylphenyl)methanol

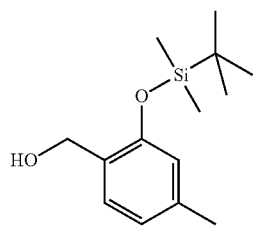 [SMILES: Cc1ccc(CO)c(O[Si](C)(C)C(C)(C)C)c1]

Sodium borohydride (1.67 g, 44.19 mmol) was added in small portions to a cooled (0° C.) solution of 2-{[tert-butyl(dimethyl)silyl]oxy}-4-methylbenzaldehyde (9.17 g, 36.60 mmol) in methanol (50 mL). The mixture was stirred until it reached room temperature as the ice bath expired. The reaction was quenched by the addition of a solution of saturated ammonium chloride. Ethyl acetate and water was added, the aqueous phase was extracted with ethyl acetate, the combined organic phases were dried over magnesium sulfate, filtered, and the solvent was evaporated under reduced pressure to give 8.97 g (97% yield) of the title compound. $^1$H NMR (400 MHz, DMSO-d$_6$) δ ppm 0.15-0.22 (m, 6H) 0.93-1.01 (m, 9H) 2.24 (s, 3H) 4.44 (d, J=5.31 Hz, 2H) 4.92 (t, J=5.56 Hz, 1H) 6.58 (d, J=0.51 Hz, 1H) 6.75 (d, J=7.58 Hz, 1H) 7.24 (d, J=7.58 Hz, 1H).

Intermediate 11 tert-Butyl[2-({[tert-butyl(dimethyl)silyl]oxy}methyl)-5-(trifluoromethyl)phenoxy]dimethylsilane

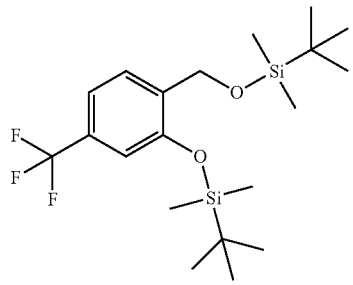 [SMILES: CC(C)(C)[Si](C)(C)OCc1ccc(C(F)(F)F)cc1O[Si](C)(C)C(C)(C)C]

tert-Butyldimethylchlorosilane (4.06 g, 26.93 mmol) was added to a solution of 2-(hydroxymethyl)-5-(trifluoromethyl)phenol (2.07 g, 10.77 mmol) and imidazole (1.83 g, 26.93 mmol) in DMF (20 mL) at 0° C., the reaction mixture was then allowed to reach r.t. and stirred over night. The reaction was partioned between ethylacetate and brine, the organic layer was dried over magnesium sulfate and filtered and concentrated to give 5.25 g of the title compound that was used in the next step without further purification. $^1$H NMR (500 MHz, CHLOROFORM-d) δ ppm 0.11-0.13 (m, 6H) 0.23-0.30 (m, 6H) 0.95-0.98 (m, 9H) 1.00-1.05 (m, 9H) 4.77 (s, 1H) 6.95 (d, 1H) 7.25 (d, 1H) 7.58 (d, 1H).

Intermediate 12

[2-{[tert-Butyl(dimethyl)silyl]oxy}-4-(trifluoromethyl)phenyl]methanol

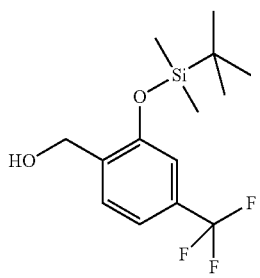 [SMILES: CC(C)(C)[Si](C)(C)Oc1cc(C(F)(F)F)ccc1CO]

To a solution of tert-butyl[2-({[tert-butyl(dimethyl)silyl]oxy}methyl)-5-(trifluoromethyl)phenoxy]dimethylsilane (5.25 g, 12.49 mmol) dissolved in MeOH (25 mL) pyridine hydrobromide perbromide (0.20 g, 0.62 mmol) was added at 0° C., the reaction mixture was stirred for 2 h. The reaction mixture was quenched with saturated aq NaHCO$_3$ solution. The aqueous layer was then extracted with EtOAc. The organic layer was dried over magnesium sulphate and concentrated. Purification by silica gel chromatography using 33-50% EtOAc in heptane+1% TEA gave 2.99 g (78% yield) of the title compound over 2 steps (from Intermediate 11). $^1$H NMR (500 MHz, CHLOROFORM-d) δ ppm 0.27-0.31 (m, 6H) 1.02-1.07 (m, 9H) 4.73 (s, 2H) 7.02 (d, 1H) 7.24 (dd, 1H) 7.48 (d, 1H).

Intermediate 13

[5-Bromo-2-(bromomethyl)phenoxy](tert-butyl)dimethylsilane

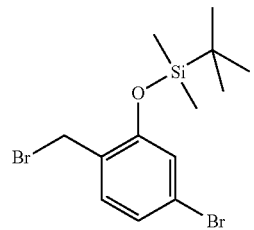 [SMILES: CC(C)(C)[Si](C)(C)Oc1cc(Br)ccc1CBr]

To a cold 0° C. solution of triphenylphosphine (4.34 g, 16.55 mmol) in DMF (60 mL) bromine (0.85 mL, 16.55 mmol) was added dropwise plus an extra drop to keep a persistent reddish tint to the solution under argon atmosphere. In this reaction mixture (4-bromo-2-{[tert-butyl(dimethyl)silyl]oxy}phenyl)methanol (5 g, 15.75 mmol) was dissolved in DMF (20 ml) added dropwise under 30 min. stirred at r.t over the weekend. The crude was dissolved in brine and extracted with EtOAc three times. The combined organic phases were washed 10% sodium thiosulfate solution and water, dried and concentrated. Purification by chromatography on silica using gradient elution 5-100% EtOAc in heptane gave 5.11 g (85% yield) of the title compound. $^1$H NMR (500 MHz, DMSO-d$_6$) δ ppm 0.28 (s, 6H) 1.02 (s, 9H) 4.58 (s, 2H) 6.99 (d, 1H) 7.17 (dd, 1H) 7.39 (d, 1H).

Intermediate 14

[2-(Bromomethyl)-5-chlorophenoxy](tert-butyl)dimethylsilane

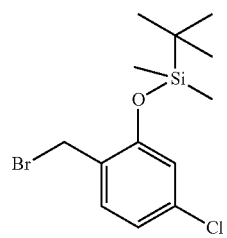 [SMILES: CC(C)(C)[Si](C)(C)Oc1cc(Cl)ccc1CBr]

The title compound was prepared following the procedure for Intermediate 13, starting from (2-{[tert-butyl(dimethyl)silyl]oxy}-4-chlorophenyl)methanol, triphenylphosphine (1.21 g, 4.62 mmol) and bromine (0.24 mL, 4.62 mmol) and DMF (30 mL). Purification by chromatography on silica using gradient elution 20% EtOAc in heptane+0.5% TEA gave 1.36 g (92% yield) of the title compound. $^1$H NMR (500 MHz, CHLOROFORM-d) δ ppm 0.28-0.37 (m, 6H) 1.04-1.10 (m, 9H) 4.48 (s, 2H) 6.81 (d, 1H) 6.92 (dd, 1H) 7.23-7.28 (m, 2H).

Intermediate 15

[2-(Bromomethyl)-5-fluorophenoxy](tert-butyl)dimethylsilane

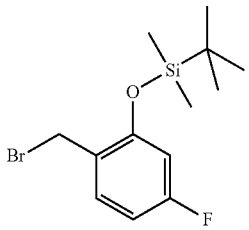 [SMILES: CC(C)(C)[Si](C)(C)Oc1cc(F)ccc1CBr]

The title compound was prepared following the procedure for Intermediate 13, starting from (2-{[tert-butyl(dimethyl)silyl]oxy}-4-fluorophenyl)methanol (1.36 g, 5.30 mmol), triphenylphosphine (1.46 g, 5.57 mmol) and bromine (0.285 ml, 5.57 mmol) in DMF (25 mL) gave 0.55 g (32.3% yield) of the title compound. $^1$H NMR (500 MHz, CHLOROFORM-d) δ ppm 0.31-0.32 (m, 6H) 1.05-1.08 (m, 9H) 4.50 (s, 2H) 6.54 (dd, J=10.25, 2.36 Hz, 1H) 6.66 (dd, 1=8.35, 2.36 Hz, 1H) 7.29 (dd, J=8.51, 6.62 Hz, 1H) MS GCMS m/z 319 [M−H]$^-$.

Intermediate 16

[2-(Bromomethyl)-5-methylphenoxy](tert-butyl)dimethylsilane

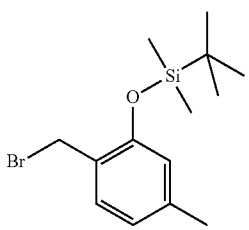 [SMILES: Cc1ccc(CBr)c(O[Si](C)(C)C(C)(C)C)c1]

Phosphorus tribromide (0.65 mL, 6.94 mmol) was added dropwise to a cooled (0° C.) solution of (2-{[tert-butyl(dimethyl)silyl]oxy}-4-methylphenyl)methanol (1.95 g, 7.71 mmol) and pyridine (0.56 mL, 6.93 mmol) in dichloromethane (10 mL). The mixture was stirred until it reached room temperature as the ice bath expired over night. Dichloromethane and brine was added and the aqueous phase was extracted with dichloromethane. The combined organic phases were washed with brine, dried over magnesium sulfate and the solvent was evaporated to give 2.25 g (93% yield) of the title compound, which was used in the next step without purification. $^1$H NMR (500 MHz, DMSO-d$_6$) δ ppm 0.25-0.28 (m, 6H) 1.01-1.04 (m, 9H) 2.26 (s, 3H) 4.59 (s, 2H) 6.67 (s, 1H) 6.75 (d, J=7.57 Hz, 1H) 7.27 (d, J=7.57 Hz, 1H).

Intermediate 17

[2-(Bromomethyl)-5-(trifluoromethyl)phenoxy](tert-butyl)dimethylsilane

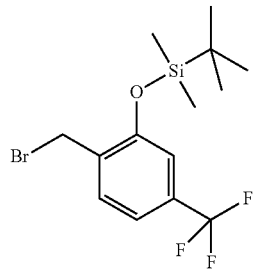 [SMILES: CC(C)(C)[Si](C)(C)Oc1cc(C(F)(F)F)ccc1CBr]

The title compound was prepared following the procedure for Intermediate 13, starting from [2-{[tert-butyl(dimethyl)silyl]oxy}-4-(trifluoromethyl)phenyl]methanol (2.18 g, 7.11 mmol), triphenylphosphine (1.96 g, 7.47 mmol), bromine (0.43 mL, 8.39 mmol) and DMF (18 mL) Purification by chromatography on silica using gradient elution 25% EtOAc in heptane+1% TEA gave 1.26 g (48% yield) of the title compound. $^1$H NMR (500 MHz, CHLOROFORM-d) δ ppm 0.31-0.35 (m, 6H) 1.05-1.10 (m, 9H) 4.51 (s, 2H) 7.03 (s, 1H) 7.19 (d, 1H) 7.45 (d, 1H).

Intermediate 18

2-({[2-(4-Bromo-2-{[tert-butyl(dimethyl)silyl]oxy}phenyl)ethyl]sulfonyl}amino)-N-tert-butylbenzenesulfonamide

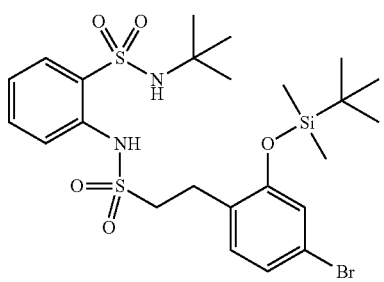 [SMILES: CC(C)(C)NS(=O)(=O)c1ccccc1NS(=O)(=O)CCc1ccc(Br)cc1O[Si](C)(C)C(C)(C)C]

A solution of N-tert-butyl-2-[(methylsulfonyl)amino]benzenesulfonamide (5 g, 16.32 mmol) in tetrahydrofuran (25 mL) was treated at −78° C. with lithium diisopropylamide (26.1 mL, 52.22 mmol). After 10 minutes, a solution of [5-bromo-2-(bromomethyl)phenoxy](tert-butyl)dimethylsilane (6.20 g, 16.32 mmol) in THF (15 mL) was added dropwise during 5 min. The reaction mixture was stirred at −78° C., for 90 min and was then allowed to reach room temperature, while stirring was continued over night. The reaction mixture was quenched with brine and the mixture was extracted with ethyl acetate. The phases were separated and the organic layer was washed with brine, dried over magnesium sulfate, filtered and concentrated under reduced pressure. Purification by chromatography on silica using gradient elution 0-50% EtOAc in heptane gave 3.64 g (37% yield) of the title compound. $^1$H NMR (500 MHz, DMSO-d$_6$) δ ppm 0.16-0.20 (m, 6H) 0.89 (s, 10H) 1.07 (s, 9H) 1.06-1.06 (m, 1H) 2.92-2.98 (m, 2H) 3.43-3.49 (m, 2H) 6.90

(d, J=1.89 Hz, 1H) 7.06-7.10 (m, 1H) 7.11-7.16 (m, 1H) 7.31 (t, J=8.20 Hz, 1H) 7.61 (m, J=7.25, 1.26 Hz, 1H) 7.65-7.68 (m, 1H) 7.88 (dd, J=8.04, 1.42 Hz, 1H) 7.99 (s, 1H) 8.77 (s, 1H); MS (ES⁻) m/z 605, 607 [M−H]⁻.

Intermediate 19

N-tert-butyl-2-({[2-(6-{[tert-butyl(dimethyl)silyl]oxy}-4-chlorocyclohexa-1,5-dien-1-yl)ethyl]sulfonyl}amino)benzenesulfonamide

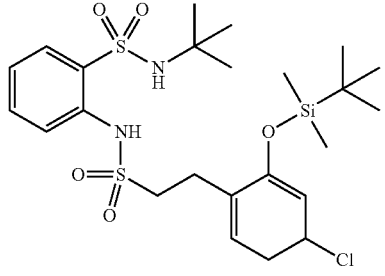 [SMILES: CC(C)(C)NS(=O)(=O)c1ccccc1NS(=O)(=O)CCC1=CCC(Cl)C=C1O[Si](C)(C)C(C)(C)C]

A solution of N-tert-butyl-2-[(methylsulfonyl)amino]benzenesulfonamide (4.56 g, 14.89 mmol) was treated at −78° C. with lithium diisopropylamide (23.83 mL, 47.66 mmol). After 10 minutes, a solution of [2-(bromomethyl)-5-chlorophenoxy](tert-butyl)dimethylsilane (5.0 g, 14.89 mmol) in THF (4 mL) was added dropwise under 1 h. The reaction mixture was stirred at −78° C. for 2 h. The reaction mixture was quenched with brine and ethyl acetate was added. The phases were separated and the organic layer was washed with brine, dried over magnesium sulfate, filtered and concentrated under reduced pressure. Purification by chromatography on silica using gradient elution 12-25% EtOAc in heptane gave 5.4 g (65% yield) of the title compound. ¹H NMR (500 MHz, DMSO-d₆) δ ppm 0.10-0.27 (m, 6H) 0.90 (s, 9H) 1.07 (s, 9H) 2.92-3.01 (m, 2H) 3.39-3.52 (m, 2H) 6.78 (d, 1H) 6.96 (dd, 1H) 7.19 (d, 1H) 7.31 (t, 1H) 7.54-7.64 (m, 1H) 7.64-7.70 (m, 1H) 7.88 (d, 1H) 7.99 (s, 1H) 8.77 (s, 1H); m/z 559, 561, 563 [M−H]⁻.

Intermediate 20

N-tert-Butyl-2-({[2-(2-{[tert-butyl(dimethyl)silyl]oxy}-4-fluorophenyl)ethyl]sulfonyl}amino)benzenesulfonamide

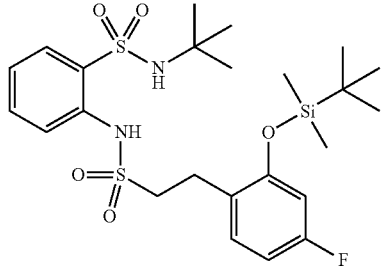 [SMILES: CC(C)(C)NS(=O)(=O)c1ccccc1NS(=O)(=O)CCc1ccc(F)cc1O[Si](C)(C)C(C)(C)C]

The title compound was prepared following the procedure for Intermediate 18 staring from N-tert-butyl-2-[(methylsulfonyl)amino]benzenesulfonamide (2.21 g, 7.20 mmol), lithium diisopropylamide (11.53 mL, 23.05 mmol) in tetrahydrofuran (25 mL) and [2-(bromomethyl)-5-fluorophenoxy](tert-butyl)dimethylsilane (2.3 g, 7.20 mmol) in tetrahydrofuran (25 mL). Purification by chromatography on silica using gradient elution 0-50% EtOAc in heptane gave 2.5 g (64% yield) of the title compound. MS (ES⁻) m/z 543 [M−H]⁻.

Intermediate 21

N-tert-Butyl-2-({[2-(2-{[tert-butyl(dimethyl)silyl]oxy}-4-methylphenyl)ethyl]sulfonyl}amino)benzenesulfonamide

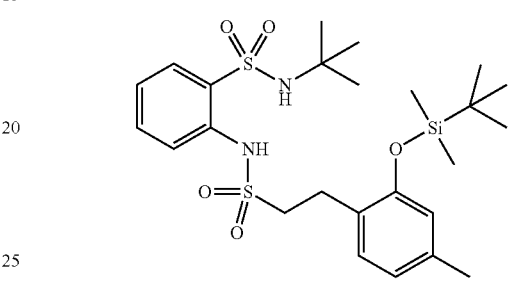

The title compound was prepared following the procedure for Intermediate 18 staring from N-tert-butyl-2-[(methylsulfonyl)amino]benzenesulfonamide (2.19 g, 7.13 mmol) in tetrahydrofuran (20 mL), lithium diisopropylamide in THF/heptane/ethylbenzene (10.71 mL, 21.42 mmol and [2-(bromomethyl)-5-methylphenoxy](tert-butyl)dimethylsilane (2.25 g, 7.14 mmol) in tetrahydrofuran (20 mL). Water and ethyl acetate were added to the reaction mixture. The aqueous phase was extracted with ethyl acetate and the combined organic phases were washed with water and brine, dried over sodium sulfate and the solvent was evaporated to give 3.81 g (99% yield) of the title compound, which was used in the next step without further purification.

Intermediate 22

N-tert-Butyl-2-[({2-[2-{[dimethyl(propan-2-yl)silyl]oxy}-4-(trifluoromethyl)phenyl]ethyl}sulfonyl)amino]benzenesulfonamide

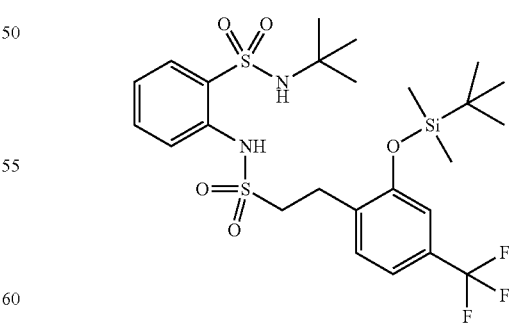

A solution of N-tert-butyl-2-[(methylsulfonyl)amino]benzenesulfonamide (0.86 g, 2.81 mmol) in THF (14 mL) was treated at −78° C. with lithium diisopropylamide (4.50 mL, 9.00 mmol). After 10 min, a solution of [2-(bromomethyl)-5-(trifluoromethyl)phenoxy](tert-butyl)dimethylsilane (1.35 g, 3.66 mmol) in THF (4 mL) was added dropwise under 8 min. The reaction mixture was stirred at −78° C., for 1 h and 15 min and then allowed to reach room temperature followed by stirring for another 1.5 h at room temperature. The reaction mixture was quenched with brine and ethyl acetate was added. The phases were separated and the organic layer was washed with brine, dried over magnesium sulfate, filtered and concentrated under reduced pressure. The title compound was used in the next step without further purification. MS (ES⁻) m/z 523, 525 [M−H]⁻.

Intermediate 23

2-({[2-(4-Bromo-2-hydroxyphenyl)ethyl]sulfonyl}amino)-N-tert-butylbenzenesulfonamide

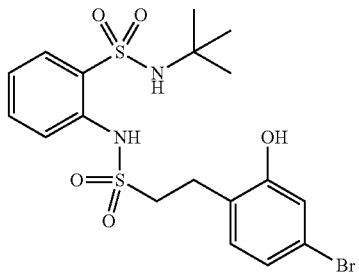 [SMILES: CC(C)(C)NS(=O)(=O)c1ccccc1NS(=O)(=O)CCc1ccc(Br)cc1O]

To a cold (0° C.) solution of 2-({[2-(4-bromo-2-{[tert-butyl(dimethyl)silyl]oxy}phenyl)ethyl]sulfonyl}amino)-N-tert-butylbenzenesulfonamide (1.01 g, 1.67 mmol) in THF (15 mL) was tetrabutylammonium fluoride (2.0 mL, 2.0 mmol, 1 M in THF) added and the reaction mixture was stirred for 3 h. The reaction mixture was quenched by addition of saturated brine and extracted with ethylacetate, the organic layer was washed with saturated aqueous NH₄Cl, dried over magnesium sulfate, filtered and concentrated under reduced pressure followed by purification by preparative HPLC. The organic solvent was evaporated and the remaining aqueous phase was extracted twice with ethyl acetate. The combined organic extracts were washed with brine, dried over magnesium sulfate, filtered and the solvent was evaporated to give 0.44 g (53% yield) of the title compound. ¹H NMR (500 MHz, DMSO-d₆) δ ppm 1.09 (s, 9H) 2.88-2.94 (m, 2H) 3.47-3.53 (m, 2H) 6.88 (dd, 1H) 6.91 (d, 1H) 7.02 (d, 1H) 7.28-7.33 (m, 1H) 7.59-7.64 (m, 1H) 7.66-7.69 (m, 1H) 7.89 (dd, 1H) 8.02 (s, 1H) 8.78 (s, 1H) 10.04 (s, 1H); MS (ES⁻) m/z 489, 491 [M−H]⁻.

Intermediate 24

N-tert-Butyl-2-({[2-(4-chloro-2-hydroxyphenyl)ethyl]sulfonyl}amino)benzenesulfonamide

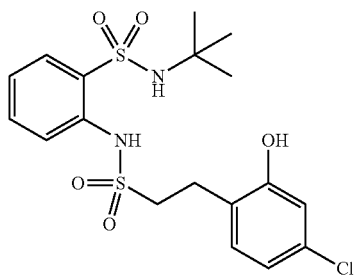 [SMILES: CC(C)(C)NS(=O)(=O)c1ccccc1NS(=O)(=O)CCc1ccc(Cl)cc1O]

The title compound was prepared following the procedure for Intermediate 23 staring from N-tert-butyl-2-({[2-(6-{[tert-butyl(dimethyl)silyl]oxy}-4-chlorocyclohexa-1,5-dien-1-yl)ethyl]sulfonyl}amino)benzenesulfonamide (0.34 g, 0.61 mmol) in THF (10 mL) and tetrabutylammonium fluoride (1.0 M solution in THF, 0.73 mL, 0.73 mmol). The reaction mixture was stirred for 2 h at 0° C. Purification by chromatography on silica using gradient elution 30-50% EtOAc in heptane gave 0.19 g (71% yield) of the title compound. ¹H NMR (500 MHz, DMSO-d₆) δ ppm 1.05-1.15 (m, 11H) 2.89-2.96 (m, 2H) 3.46-3.54 (m, 2H) 6.75 (dd, 1H) 6.77 (d, 1H) 7.08 (d, 1H) 7.30 (t, 1H) 7.55-7.65 (m, 1H) 7.65-7.73 (m, 1H) 7.89 (d, 1H) 8.02 (s, 1H) 8.78 (s, 1H) 10.04 (s, 1H); MS (ES⁻) m/z 445, 447, 449 [M−H]⁻.

Intermediate 25

N-tert-butyl-2-({[2-(4-fluoro-2-hydroxyphenyl)ethyl]sulfonyl}amino)benzenesulfonamide

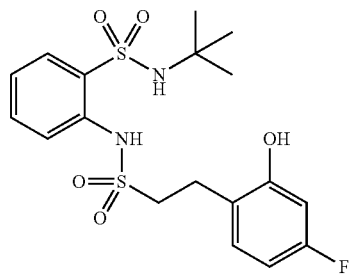 [SMILES: CC(C)(C)NS(=O)(=O)c1ccccc1NS(=O)(=O)CCc1ccc(F)cc1O]

The title compound was prepared following the procedure for Intermediate 23 starting from N-tert-butyl-2-({[2-(2-{[tert-butyl(dimethyl)silyl]oxy}-4-fluorophenyl)ethyl]sulfonyl}amino)benzenesulfonamide (2.5 g, 4.59 mmol) in THF (15 mL) and tetrabutylammonium fluoride (5.51 ml, 5.51 mmol, 1 M in THF). Purification by chromatography on silica using gradient elution 0-50% EtOAc in heptane gave 0.95 g (48% yield) of the title compound. MS (ES⁻) m/z 429 [M−H]⁻.

Intermediate 26

N-tert-Butyl-2-({[2-(2-hydroxy-4-methylphenyl)ethyl]sulfonyl}amino)benzenesulfonamide

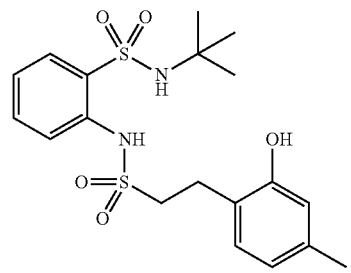 [SMILES: Cc1ccc(CCS(=O)(=O)Nc2ccccc2S(=O)(=O)NC(C)(C)C)c(O)c1]

The title compound was prepared following the procedure for Intermediate 23 staring from N-tert-butyl-2-({[2-(2-{[tert-butyl(dimethyl)silyl]oxy}-4-methylphenyl)ethyl]sulfonyl}amino)benzenesulfonamide (3.76 g, 6.94 mmol) in anhydrous tetrahydrofuran (25 mL) and tetrabutylammonium fluoride (8.5 mL, 8.50 mmol, 1 M in THF). The reaction mixture was stirred for 1 h at 0° C. Purification by chromatography on silica using gradient elution 5-80% EtOAc in heptane gave 0.76 g (25.5% yield) the title compound calculated over 2 steps starting from Intermediate 21. ¹H NMR (400 MHz, DMSO-d₆) δ ppm 1.09 (s, 9H) 2.15 (s, 3H) 2.84-2.93 (m, 2H) 3.46 (m, J=7.83 Hz, 2H) 6.49 (dd, J=7.58, 0.76 Hz, 1H) 6.56 (s, 1H) 6.89 (d, J=7.58 Hz, 1H) 7.30 (t, J=7.45 Hz, 1H) 7.57-7.72 (m, 2H) 7.88 (d, J=7.58 Hz, 1H) 8.04 (s, 1H) 8.76 (s, 1H) 9.38 (s, 1H). MS (ES⁻) m/z 425 [M−H]⁻.

Intermediate 27

N-tert-butyl-2-[({2-[2-hydroxy-4-(trifluoromethyl)phenyl]ethyl}sulfonyl)amino]benzenesulfonamide

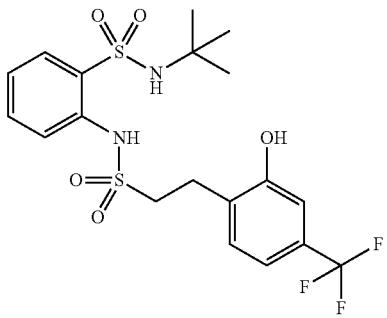 [SMILES: CC(C)(C)NS(=O)(=O)c1ccccc1NS(=O)(=O)CCc1ccc(C(F)(F)F)cc1O]

The title compound was prepared following the procedure for Intermediate 23 staring from N-tert-butyl-2-[({2-[2-{[dimethyl(propan-2-yl)silyl]oxy}-4-(trifluoromethyl)phenyl]ethyl}sulfonyl)amino]benzenesulfonamide (1.67 g, 2.81 mmol) in THF (15 mL) and tetrabutylammonium fluoride (2.81 mL, 2.81 mmol, 1.0 M in THF). The reaction mixture was stirred for 2 h at 0° C. Purification by chromatography on silica using gradient elution 30-50% EtOAc in heptane, followed by 100% EtOAc and followed by a second purification by silica gel chromatography using 50% EtOAc in heptane followed by 100% EtOAc gave 0.91 g (67% yield) of the title compound. MS (ES⁻) m/z 479 [M−H]⁻.

Intermediate 28

2-[({2-[4-Bromo-2-(tetrahydro-2H-pyran-4-ylmethoxy)phenyl]ethyl}sulfonyl)amino]-N-tert-butyl-benzenesulfonamide

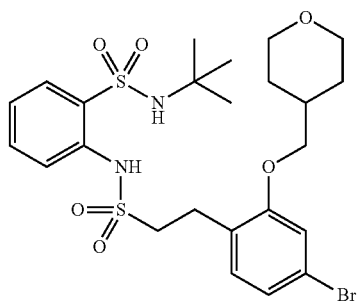 [SMILES: CC(C)(C)NS(=O)(=O)c1ccccc1NS(=O)(=O)CCc1ccc(Br)cc1OCC1CCOCC1]

2-({[2-(4-Bromo-2-hydroxyphenyl)ethyl]sulfonyl}amino)-N-tert-butylbenzenesulfonamide (3.2 g, 6.51 mmol) and 4-(bromomethyl)tetrahydro-2H-pyran (3.50 g, 19.54 mmol) were added to a solution of cesium carbonate (6.36 g, 19.54 mmol) in THF (10 mL) and the reaction mixture was heated using MW at 110° C., for 2 h. The reaction mixture was diluted with NH₄Cl (aq) and extracted with EtOAc two times, washed with water and concentrated. Purification by chromatography on silica using gradient elution of 0-50% EtOAc in n-heptane gave 3.0 g (78% yield) of the title compound. ¹H NMR (500 MHz, DMSO-d₆) δ ppm 1.06-1.10 (m, 9H) 1.17-1.27 (m, 2H) 1.53 (br. s., 2H) 1.81-1.92 (m, 1H) 2.91-2.98 (m, 2H) 3.25 (d, J=1.58 Hz, 2H) 3.45-3.54 (m, 2H) 3.77-3.85 (m, 4H) 7.05 (d, J=1.58 Hz, 1H) 7.10-7.14 (m, 3H) 7.32 (s, 1H) 7.59-7.70 (m, 3H) 7.89 (dd, J=8.04, 1.10 Hz, 1H) 8.01 (s, 1H) 8.77 (s, 1H); MS m/z 589, 590 [M−H]⁻.

Intermediate 29

N-tert-Butyl-2-[({2-[4-chloro-2-(tetrahydro-2H-pyran-4-ylmethoxy)phenyl]ethyl}sulfonyl)amino]benzenesulfonamide

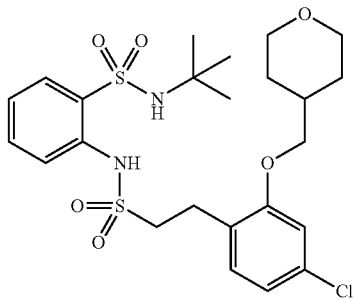 [SMILES: CC(C)(C)NS(=O)(=O)c1ccccc1NS(=O)(=O)CCc1ccc(Cl)cc1OCC1CCOCC1]

The title compound was prepared following the procedure for Intermediate 28, starting from 4-(bromomethyl)tetrahydro-2H-pyran (0.16 g, 0.89 mmol) and N-tert-butyl-2-({[2-(4-chloro-2-hydroxyphenyl)ethyl]sulfonyl}amino)benzenesulfonamide (0.20 g, 0.45 mmol) with cesium carbonate (0.22 g, 0.67 mmol) in DMF (3 mL). Purification by chromatography on silica using gradient elution 16-50% EtOAc in heptane gave 126.4 mg (52% yield) of the title compound. ¹H NMR (500 MHz, DMSO-d₆) δ ppm 1.03-1.13 (m, 9H) 1.17-1.32 (m, 2H) 1.48-1.64 (m, 2H) 1.79-1.94 (m, 1H) 2.89-3.04 (m, 2H) 3.25 (td, 2H) 3.44-3.55 (m, 2H) 3.75-3.87 (m, 4H) 6.91 (dd, 1H) 7.00 (d, 1H) 7.17 (d, 1H) 7.27-7.37 (m, 1H) 7.58-7.70 (m, 2H) 7.89 (dd, 1H) 8.01 (s, 1H) 8.77 (s, 1H); MS (ES⁻) m/z 543, 545, 547 [M−H]⁻.

Intermediate 30

N-tert-Butyl-2-[({2-[4-fluoro-2-(tetrahydro-2H-pyran-4-ylmethoxy)phenyl]ethyl}sulfonyl)amino]benzenesulfonamide

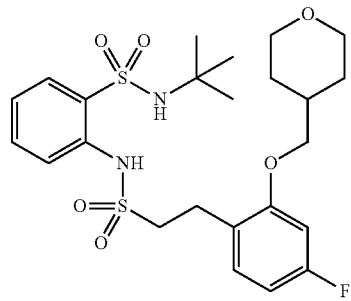 [SMILES: CC(C)(C)NS(=O)(=O)c1ccccc1NS(=O)(=O)CCc1ccc(F)cc1OCC1CCOCC1]

The title compound was prepared following the procedure for Intermediate 28 starting from N-tert-butyl-2-({[2-(4-fluoro-2-hydroxyphenyl)ethyl]sulfonyl}amino)benzenesulfonamide (0.20 g, 0.46 mmol) and 4-(bromomethyl)tetrahydro-2H-pyran (250 mg, 1.39 mmol) with cesium carbonate (454 mg, 1.39 mmol) in THF (5 mL). Purification by chromatography on silica using gradient elution 16-50% EtOAc in heptane gave 60 mg (24% yield) of the title compound. MS (ES$^-$) m/z 527 [M–H]$^-$.

Intermediate 31

N-tert-Butyl-2-[({2-[4-methyl-2-(tetrahydro-2H-pyran-4-ylmethoxy)phenyl]ethyl}sulfonyl)amino]benzenesulfonamide

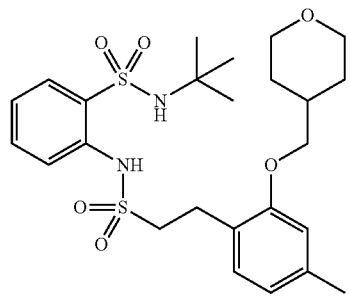 [SMILES: Cc1ccc(CCS(=O)(=O)Nc2ccccc2S(=O)(=O)NC(C)(C)C)c(OCC2CCOCC2)c1]

The title compound was prepared following the procedure for Intermediate 28 starting from N-tert-butyl-2-({[2-(2-hydroxy-4-methylphenyl)ethyl]sulfonyl}amino)benzenesulfonamide (0.20 g, 0.48 mmol), and 4-(bromomethyl)tetrahydro-2H-pyran ((0.35 mL, 0.48 mmol) with cesium carbonate (0.62 g, 1.92 mmol), in DMF (5 mL). Purification by chromatography on silica using gradient elution 0-80% EtOAc in heptane gave 0.25 g (100% yield) of the title compound. MS (ES$^-$) m/z 523 [M–H]$^-$.

Intermediate 32

N-tert-butyl-2-[({2-[2-(tetrahydro-2H-pyran-4-ylmethoxy)-4-(trifluoromethyl)phenyl]ethyl}sulfonyl)amino]benzenesulfonamide

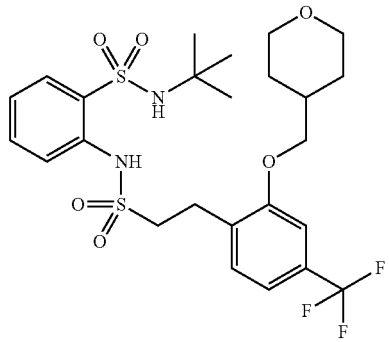 [SMILES: CC(C)(C)NS(=O)(=O)c1ccccc1NS(=O)(=O)CCc1ccc(C(F)(F)F)cc1OCC1CCOCC1]

The title compound was prepared following the procedure for Intermediate 28 starting from N-tert-butyl-2-[({2-[2-hydroxy-4-(trifluoromethyl)phenyl]ethyl}sulfonyl)amino]benzenesulfonamide (0.46 g, 0.95 mmol), and 4-(bromomethyl)tetrahydro-2H-pyran (0.34 g, 1.89 mmol) with cesium carbonate (0.46 g, 1.42 mmol), in DMF (3 mL). Purification by chromatography on silica using gradient elution 33-50% EtOAc in heptane gave 0.18 g (33% yield) of the title compound. $^1$H NMR (600 MHz, DMSO-d$_6$) δ ppm 1.05-1.10 (m, 9H) 1.26 (qd, 2H) 1.58 (d, 2H) 1.89 (dd, 1H) 3.05 (br. s., 2H) 3.27 (t, 2H) 3.52-3.60 (m, 2H) 3.83 (dd, 2H) 3.86 (d, 2H) 7.18-7.24 (m, 2H) 7.32 (t, 1H) 7.39 (d, 1H) 7.58-7.65 (m, 1H) 7.65-7.69 (m, 1H) 7.89 (d, 1H) 7.99 (s, 1H) 8.79 (s, 1H); MS (ES$^-$) m/z 577 [M–H]$^-$.

Intermediate 33

(4,4-Difluorocyclohexyl)methyl methanesulfonate

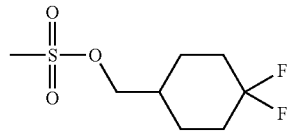

To (4,4-difluorocyclohexyl)methanol (3.66 g, 24.37 mmol) anhydrous dichloromethane (13 mL) was added and the solution was cooled to 0° C. Triethylamine (4.07 mL, 29.25 mmol) was added followed by dropwise addition of methanesulfonyl chloride (2.26 mL, 29.25 mmol). The reaction mixture was stirred at room temperature for 1 h. The reaction progress was monitored by GC. An aqueous solution of saturated sodium hydrogen carbonate was added, the two phases were separated and the aqueous phase was extracted with dichloromethane two times. The combined organic extracts were washed with brine, dried over magnesium sulfate, filtered and the solvent was evaporated to give 5.29 g (95% yield) of the title compound. $^1$H NMR (400 MHz, CHLOROFORM-d) δ ppm 1.36-1.45 (m, 2H) 1.65-1.94 (m, 5H) 2.10-2.21 (m, 2H) 3.03 (s, 3H) 4.09 (d, 2H).

Intermediate 34

N-tert-Butyl-2-{[(2-{4-chloro-2-[(4,4-difluorocyclohexyl)methoxy]phenyl}ethyl)sulfonyl]amino}benzenesulfonamide

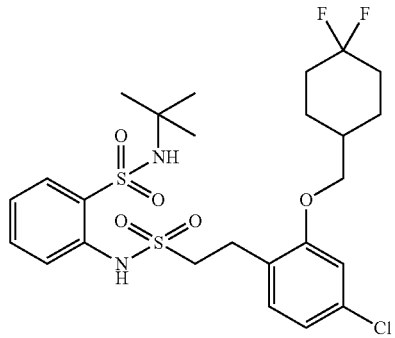 [SMILES: CC(C)(C)NS(=O)(=O)c1ccccc1NS(=O)(=O)CCc1ccc(Cl)cc1OCC1CCC(F)(F)CC1]

A mixture of N-tert-butyl-2-({[2-(4-chloro-2-hydroxyphenyl)ethyl]sulfonyl}amino)benzenesulfonamide (459 mg, 1.03 mmol), potassium carbonate (284 mg, 2.05 mmol), (4,4-difluorocyclohexyl)methyl methanesulfonate (469 mg, 2.05 mmol) and acetonitrile (5 mL), was heated at 75° C. for 24 h. An additional portion of (4,4-difluorocyclohexyl) methyl methanesulfonate (336 mg, 1.47 mmol) was added and the stirring was continued. The solvent was evaporated and the crude product was dissolved in ethyl acetate. The organic phase was washed with water, brine, dried over magnesium sulfate, filtered and the solvent was evaporated. Purification by chromatography on silica using gradient elution 5-50% EtOAc in heptane, followed by purification by preparative-HPLC gave 0.17 g (28 5 yield) of the title compound. $^1$H NMR (500 MHz, DMSO-$d_6$) δ ppm 1.08 (s, 9H) 1.19-1.29 (m, 2H) 1.76 (m, 5H) 1.94-2.04 (m, 2H) 2.96 (m, 2H) 3.49 (m, 2H) 3.82 (d, 2H) 6.91 (dd, 1H) 7.01 (d, 1H) 7.17 (d, 1H) 7.30-7.34 (m, 1H) 7.63 (m, 2H) 7.89 (dd, 1H) 8.01 (s, 1H) 8.78 (s, 1H). MS (ES$^-$) m/z 577, 579 [M–H]$^-$.

Intermediate 35

N-tert-Butyl-2-{[(2-{2-[(4,4-difluorocyclohexyl)methoxy]-4-fluorophenyl}ethyl)sulfonyl]amino}benzenesulfonamide The title compound was prepared following the procedure for Intermediate 34 starting from N-tert-butyl-2-({[2-(4-fluoro-2-hydroxyphenyl)ethyl]sulfonyl}amino)benzenesulfonamide (154 mg, 0.36 mmol), (4,4-difluorocyclohexyl)methyl methanesulfonate (327 mg, 1.43 mmol) and potassium carbonate (0.041 mL, 0.72 mmol) in acetonitrile (5 mL). Additional 4,4-difluorocyclohexyl)methyl methanesulfonate (200 mg) was added after stirring over night, to drive the reaction to completion. Purification by preparative-HPLC gave 30 mg (15% yield) of the title compound. MS (ES$^-$) m/z 561 [M–H]$^-$.

Intermediate 36

N-tert-Butyl-2-{[(2-{2-[(4,4-difluorocyclohexyl)methoxy]-4-methylphenyl}ethyl)sulfonyl]amino}benzenesulfonamide

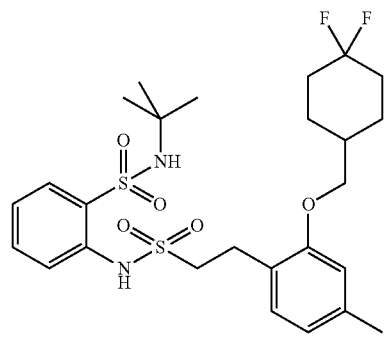 [SMILES: Cc1ccc(CCS(=O)(=O)Nc2ccccc2S(=O)(=O)NC(C)(C)C)c(OCC2CCC(F)(F)CC2)c1]

The title compound was prepared following the procedure for Intermediate 34 starting from N-tert-butyl-2-({[2-(2-hydroxy-4-methylphenyl)ethyl]sulfonyl}amino)benzenesulfonamide (191 mg, 0.45 mmol), (4,4-difluorocyclohexyl)methyl methanesulfonate (409 mg, 1.79 mmol) and potassium carbonate (124 mg, 0.90 mmol), in acetonitrile (5 mL). Additional 4,4-difluorocyclohexyl)methyl methanesulfonate (409 mg, 1.79 mmol) was added after stirring over night to drive the reaction to completion. Purification by preparative-HPLC, gave 33 mg (13% yield) of the title compound. MS (ES$^-$) m/z 557 [M–H]$^-$.

Example 1

2-[({2-[4-Bromo-2-(tetrahydro-2H-pyran-4-ylmethoxy)phenyl]ethyl}sulfonyl)amino]benzenesulfonamide

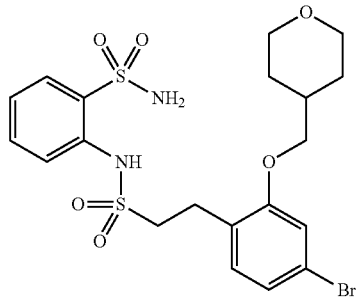 [SMILES: NS(=O)(=O)c1ccccc1NS(=O)(=O)CCc1ccc(Br)cc1OCC1CCOCC1]

2-[({2-[4-Bromo-2-(tetrahydro-2H-pyran-4-ylmethoxy)phenyl]ethyl}sulfonyl)amino]-N-tert-butylbenzenesulfonamide (2.4 g, 4.07 mmol) was dissolved in TFA (2 mL) and stirred for 1.5 hours. Purification by chromatography on silica using gradient elution 0-50% EtOAc in heptane, evaporation of the solvent, followed by dissolving the crude product in ethanol (4 mL) and adding H$_2$O (1.2 mL) under stirring resulted in precipitation which gave 1.94 g (89% yield) of the title compound after filtration and drying in vacuo. $^1$H NMR (500 MHz, DMSO-$d_6$) δ ppm 1.24 (qd, J=12.24, 4.57 Hz, 2H) 1.57 (dd, J=12.77, 1.73 Hz, 2H) 1.83-1.93 (m, 1H) 2.91-2.97 (m, 2H) 3.26 (td, J=11.66, 1.58 Hz, 2H) 3.43-3.49 (m, 2H) 3.78-3.85 (m, 4H) 7.03 (dd, J=7.88, 1.89 Hz, 1H) 7.10-7.13 (m, 2H) 7.34 (ddd, J=8.04, 6.78, 1.58 Hz, 1H) 7.58-7.66 (m, 2H) 7.81 (s, 2H) 7.87 (dd, J=7.88, 1.26 Hz, 1H) 8.90-8.95 (m, 1H)—). MS (ES$^-$) m/z 531, 533 [M–H]$^-$.

Example 2

2-[({2-[4-Chloro-2-(tetrahydro-2H-pyran-4-ylmethoxy)phenyl]ethyl}sulfonyl)amino]benzenesulfonamide

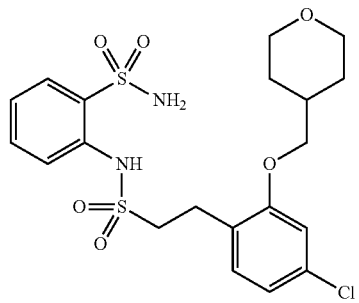 [SMILES: NS(=O)(=O)c1ccccc1NS(=O)(=O)CCc1ccc(Cl)cc1OCC1CCOCC1]

The title compound was prepared following the procedure for Example 1 starting from N-tert-butyl-2-[({2-[4-chloro-2-(tetrahydro-2H-pyran-4-ylmethoxy)phenyl]ethyl}sulfonyl)amino]benzenesulfonamide (0.124 g, 0.23 mmol) and trifluoroacetic acid (1.5 mL, 19.47 mmol). Purification by preparative-HPLC gave 76 mg (69% yield) of the title compound. $^1$H NMR (500 MHz, DMSO-$d_6$) δ ppm 1.24 (qd, 2H) 1.57 (d, 2H) 1.83-1.95 (m, 1H) 2.91-3.01 (m, 2H) 3.22-3.30 (m, 2H) 3.42-3.52 (m, 2H) 3.79 (d, 2H) 3.83 (dd, 2H) 6.90 (dd, 1H) 7.00 (d, 1H) 7.18 (d, 1H) 7.33 (t, 1H) 7.55-7.68 (m, 2H) 7.81 (br. s., 2H) 7.87 (d, 1H) 8.92 (s, 1H). MS (ES$^-$) m/z 487, 489, 491 [M–H]$^-$.

Example 3

2-[({2-[2-(Tetrahydro-2H-pyran-4-ylmethoxy)-4-(trifluoromethyl)phenyl]ethyl}sulfonyl)amino]benzenesulfonamide

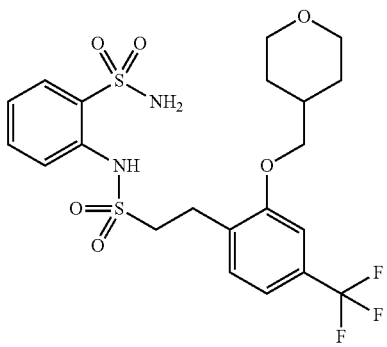 [SMILES: NS(=O)(=O)c1ccccc1NS(=O)(=O)CCc1ccc(C(F)(F)F)cc1OCC1CCOCC1]

N-tert-Butyl-2-[({2-[2-(tetrahydro-2H-pyran-4-ylmethoxy)-4-(trifluoromethyl)phenyl]ethyl}sulfonyl)amino]benzenesulfonamide (0.18 g, 0.31 mmol) was dissolved in trifluoroacetic acid (1.5 mL, 19.47 mmol) and stirred for 4 h. The reaction mixture was co-evaporated with toluene. Purification by chromatography on silica using gradient elution 4-6% methanol in chloroform, followed by a second purification by chromatography on silica using gradient elution heptane: EtOAc 2:1, 1:1, 1:2 and 1:3 gave 0.13 g (79% yield) of the title compound. $^1$H NMR (600 MHz, DMSO-$d_6$) δ ppm 1.27 (dd, 2H) 1.60 (d, 2H) 1.86-1.96 (m, 1H) 3.02-3.09 (m, 2H) 3.28 (t, 2H) 3.48-3.57 (m, 2H) 3.84 (dd, 2H) 3.87 (d, 2H) 7.16-7.23 (m, 2H) 7.33 (t, 1H) 7.39 (d, 1H) 7.57-7.67 (m, 2H) 7.80 (s, 2H) 7.87 (d, 1H) 8.94 (s, 1H). MS (ES$^-$) m/z 521 [M–H]$^-$

Example 4

2-[({2-[4-methyl-2-(tetrahydro-2H-pyran-4-ylmethoxy)phenyl]ethyl}sulfonyl)amino]benzenesulfonamide

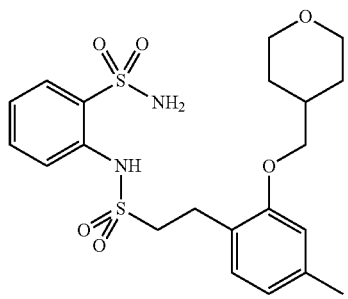 [SMILES: Cc1ccc(CCS(=O)(=O)Nc2ccccc2S(N)(=O)=O)c(OCC2CCOCC2)c1]

N-tert-Butyl-2-[({2-[4-methyl-2-(tetrahydro-2H-pyran-4-ylmethoxy)phenyl]ethyl}sulfonyl)amino]benzenesulfonamide (0.25 g, 0.48 mmol) in trifluoroacetic acid (2 mL, 25.92 mmol) was stirred at room temperature for 3 h. The TFA was evaporated, water and ethyl acetate was added and the organic phase was washed with water and brine and dried over magnesium sulfate. Purification by chromatography on silica using gradient elution 10-80% EtOAc in heptane, followed by purification by preparative HPLC gave 0.14 g (65% yield) of the title compound. $^1$H NMR (500 MHz, DMSO-$d_6$) δ 1.18-1.28 (m, 2H) 1.58 (d, J=12.61 Hz, 2H) 1.81-1.92 (m, 1H) 2.23 (s, 3H) 2.88-2.96 (m, 2H) 3.26 (t, 2H) 3.38-3.47 (m, 2H) 3.73 (d, 2H) 3.83 (dd, 2H) 6.64 (d, 1H) 6.74 (s, 1H) 7.00 (d, 1H) 7.33 (t, 1H) 7.57-7.69 (m, 2H) 7.82 (s, 2H) 7.87 (d, 1H) 8.90 (s, 1H). MS (ES$^-$) m/z 467 [M–H]$^-$.

Example 5

2-[({2-[4-Fluoro-2-(tetrahydro-2H-pyran-4-ylmethoxy)phenyl]ethyl}sulfonyl)amino]benzenesulfonamide

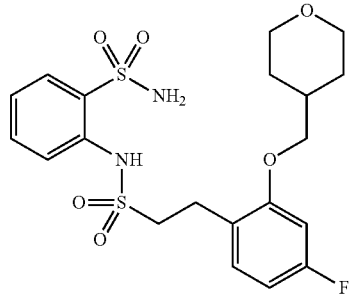 [SMILES: NS(=O)(=O)c1ccccc1NS(=O)(=O)CCc1ccc(F)cc1OCC1CCOCC1]

N-tert-Butyl-2-[({2-[4-fluoro-2-(tetrahydro-2H-pyran-4-ylmethoxy)phenyl]ethyl}sulfonyl)amino]benzenesulfonamide (60 mg, 0.11 mmol) was dissolved in TFA (2 mL) and stirred for 1.5 h. Purification by chromatography on silica using gradient elution 0-50% EtOAc in heptane, evaporation of the solvent followed by dissolving the crude product in ethanol (4 mL) and adding H$_2$O (1.2 mL) under stirring resulted in precipitation which gave 32 mg (60% yield) of the title compound after filtration and drying in vacuo. $^1$H NMR (500 MHz, CHLOROFORM-d) δ 1.46 (dd, J=13.08, 4.57 Hz, 2H) 1.69 (dd, J=12.77, 1.73 Hz, 2H) 2.00-2.09 (m, 1H) 3.17-3.21 (m, 2H) 3.41 (td, J=11.90, 2.05 Hz, 2H) 3.49-3.55 (m, 2H) 3.78 (d, J=5.99 Hz, 2H) 3.98 (dd, 1=11.19, 3.94 Hz, 2H) 5.26 (s, 2H) 6.56 (dd, J=10.72, 2.21 Hz, 1H) 6.61 (d, J=2.52 Hz, 1H) 7.12 (dd, J=8.20, 6.62 Hz, 1H) 7.30 (ddd, J=8.12, 7.01, 1.58 Hz, 1H) 7.57-7.64 (m, 2H) 7.98 (dd, 1=8.04, 1.42 Hz, 1H) 8.30 (s, 1H). MS (ES$^-$) m/z 471 [M–H]$^-$.

Example 6

2-{[(2-{4-Chloro-2-[(4,4-difluorocyclohexyl)methoxy]phenyl}ethyl)sulfonyl]amino}benzenesulfonamide

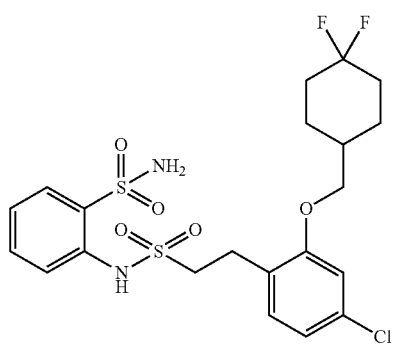 [SMILES: NS(=O)(=O)c1ccccc1NS(=O)(=O)CCc1ccc(Cl)cc1OCC1CCC(F)(F)CC1]

N-tert-butyl-2-{[(2-{4-chloro-2-[(4,4-difluorocyclohexyl)methoxy]phenyl}ethyl)sulfonyl]amino}benzenesulfonamide (165 mg, 0.28 mmol) was mixed with trifluoroacetic acid (3 mL, 38.94 mmol). The mixture was stirred at room temperature for 3 h. The trifluoroacetic acid was evaporated and the product was dissolved in ethyl acetate. The organic phase was washed with water, saturated NaHCO₃, brine, dried over magnesium sulfate, filtered and the solvent was evaporated under reduced pressure. Purification by preparative HPLC gave the 112 mg (75% yield) of title compound. ¹H NMR (500 MHz, DMSO-d₆) δ ppm 1.19-1.31 (m, 2H) 1.69-1.85 (m, 5H) 2.00 (m, 2H) 2.92-2.99 (m, 2H) 3.43-3.50 (m, 2H) 3.83 (d, 2H) 6.90 (dd, 1H) 7.01 (d, 1H) 7.17 (d, 1H) 7.33 (t, 1H) 7.58-7.66 (m, 2H) 7.82 (s, 2H) 7.87 (d, 1H) 8.93 (s, 1H)). MS (ES⁻) m/z 521, 523 [M−H]⁻.

Example 7

2-{[(2-{2-[(4,4-Difluorocyclohexyl)methoxy]-4-methylphenyl}ethyl)sulfonyl]amino}benzenesulfonamide

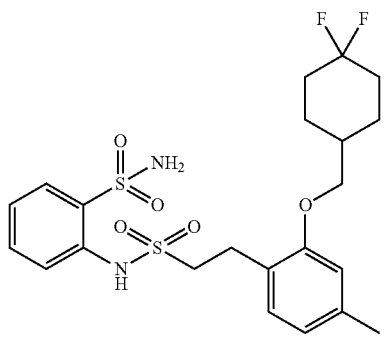 [SMILES: Cc1ccc(CCS(=O)(=O)Nc2ccccc2S(N)(=O)=O)c(OCC2CCC(F)(F)CC2)c1]

The title compound was prepared following the procedure for Example 6, starting from N-tert-butyl-2-{[(2-{2-[(4,4-difluorocyclohexyl)methoxy]-4-methylphenyl}ethyl)sulfonyl]amino}benzenesulfonamide (33 mg, 0.06 mmol) and trifluoroacetic acid (1 mL, 12.98 mmol). Purification by preparative HPLC gave 18 mg (60% yield) of the title compound. ¹H NMR (400 MHz, DMSO-d₆) δ ppm 1.17-1.31 (m, 2H) 1.80 (d, 5H) 1.95-2.06 (m, 2H) 2.23 (s, 3H) 2.92 (m, 2H) 3.76 (d, 2H) 6.60-6.67 (m, 1H) 6.74 (s, 1H) 6.99 (d, 1H) 7.16-7.34 (m, 1H) 7.45-7.95 (m, 5H); MS (ES⁻) m/z 501 [M−H]⁻.

Example 8

2-{[(2-{2-[(4,4-Difluorocyclohexyl)methoxy]-4-fluorophenyl}ethyl)sulfonyl]amino}benzenesulfonamide

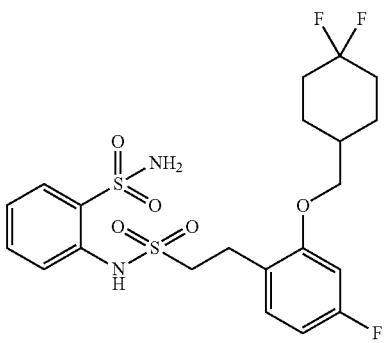 [SMILES: NS(=O)(=O)c1ccccc1NS(=O)(=O)CCc1ccc(F)cc1OCC1CCC(F)(F)CC1]

The title compound was prepared following the procedure for Example 6, starting from N-tert-butyl-2-{[(2-{2-[(4,4-difluorocyclohexyl)methoxy]-4-fluorophenyl}ethyl)sulfonyl]amino}benzenesulfonamide (30 mg, 0.05 mmol) and trifluoroacetic acid (3 mL, 38.94 mmol). Purification by preparative-HPLC gave 17 mg (63% yield) of the title compound. ¹H NMR (400 MHz, DMSO-d₆) δ ppm 1.17-1.31 (m, 2H) 1.67-1.86 (m, 5H) 1.94-2.06 (m, 2H) 2.91-2.98 (m, 2H) 3.40-3.49 (m, 2H) 3.80 (d, 2H) 6.66 (m, 1H) 6.84 (dd, 1H) 7.17 (dd, 1H) 7.29-7.36 (m, 1H) 7.56-7.67 (m, 2H) 7.78-7.90 (m, 3H) 8.92 (s, 1H). MS (ES⁻) m/z 505 [M−H]⁻.

Example 9

2-[({2-[4-(Phenylethynyl)-2-(tetrahydro-2H-pyran-4-ylmethoxy)phenyl]ethyl}sulfonyl)amino]benzenesulfonamide

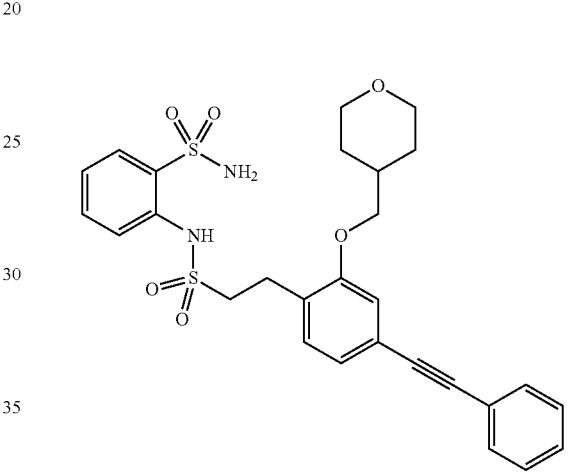

Copper(I) iodide (0.096 g, 0.50 mmol) and [1,1′-bis(diphenylphosphino)ferrocene]dichloropalladium(II) complex with dichloromethane (1:1; 0.188 g, 0.23 mmol) were added to a solution of ethynylbenzene (2.19 mL, 19.91 mmol), 2-[({2-[4-bromo-2-(tetrahydro-2H-pyran-4-ylmethoxy)phenyl]ethyl}sulfonyl)amino]benzenesulfonamide (2.25 g, 4.22 mmol) and diisopropylamine (1.87 mL, 13.33 mmol) in DMF (17.03 mL, which had been purged with nitrogen for 10 minutes) in a microwave vial. The vial was heated in the MW for 90 min at 110° C. The reaction mixture was cooled to room temperature. The reaction mixture was diluted with EtOAc (200 mL), and washed with saturated brine (125 mL). The aqueous later was separated and extracted with EtOAc (100 mL). The combined organics were dried over MgSO₄, filtered and evaporated. A two step purification sequence by chromatography on silica using gradient elution 10-40% EtOAc in heptane, followed by another silica chromatography using a elution gradient 30 to 80% Et₂O in heptane gave 1.17 g (50% yield) of the title compound. ¹H NMR (500 MHz, DMSO-d₆) δ ppm 1.19-1.34 (m, 2H) 1.58 (m, 2H) 1.91 (m, 1H) 3.01 (d, 1=7.88 Hz, 2H) 3.24-3.32 (m, 2H) 3.43-3.56 (m, 2H) 3.79-3.88 (m, 4H) 7.05 (d, J=7.57 Hz, 1H) 7.09 (s, 1H) 7.21 (d, J=7.88 Hz, 1H) 7.29-7.38 (m, 1H) 7.40-7.45 (m, 3H) 7.51-7.56 (m, 2H) 7.58-7.68 (m, 2H) 7.83 (br s, 2H) 7.85-7.93 (m, 1H) 8.94 (br s, 1H). MS (ES⁻) m/z 553 [M−H]⁻.

Example 10

2-[({2-[4-(Cyclopropylethynyl)-2-(tetrahydro-2H-pyran-4-ylmethoxy)phenyl]ethyl}sulfonyl)amino]benzenesulfonamide

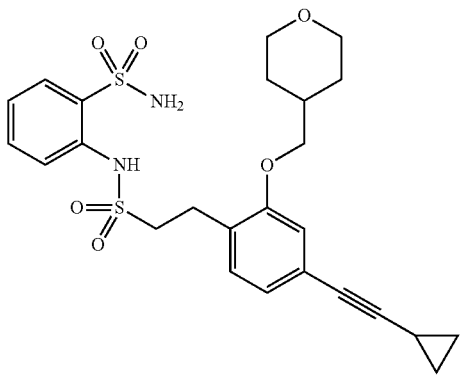 [SMILES: NS(=O)(=O)c1ccccc1NS(=O)(=O)CCc1ccc(C#CC2CC2)cc1OCC1CCOCC1]

A mixture of 2-[({2-[4-bromo-2-(tetrahydro-2H-pyran-4-ylmethoxy)phenyl]ethyl}sulfonyl)amino]benzenesulfonamide (160 mg, 0.3 mmol), copper(I) iodide (5.71 mg, 0.03 mmol), bis(triphenylphosphine)palladium(II)chloride (21.06 mg, 0.03 mmol) in DMF (3 mL), ethynylcyclopropane (0.13 mL, 1.50 mmol) and diisopropylamine (0.13 mL, 0.90 mmol) was heated in a MW at 100° C. for 2 h. The reaction mixture was partitioned between EtOAc (75 mL) and H$_2$O (25 mL)+HCl (aq., 2 M, 25 mL), the organic layer was dried (MgSO$_4$) and evaporated. Purification by preparative HPLC gave 59 mg (38% yield) of the title compound. $^1$H NMR (500 MHz, DMSO-d$_6$) δ ppm 0.64-0.75 (m, 2H), 0.82-0.92 (m, 2H), 1.23 (qd, 2H), 1.43-1.64 (m, 3H), 1.79-1.94 (m, 1H), 2.89-3.00 (m, 2H), 3.26 (t, 2H), 3.39-3.50 (m, 2H), 3.72-3.87 (m, 4H), 6.81-6.91 (m, 2H), 7.09 (d, 1H), 7.29-7.38 (m, 1H), 7.57-7.68 (m, 2H), 7.77-7.91 (m, 3H), 8.92 (s, 1H). MS (ES$^-$) m/z 517 [M−H]$^-$.

Example 11

2-[({2-[4-(Cyclopentylethynyl)-2-(tetrahydro-2H-pyran-4-ylmethoxy)phenyl]ethyl}sulfonyl)amino]benzenesulfonamide

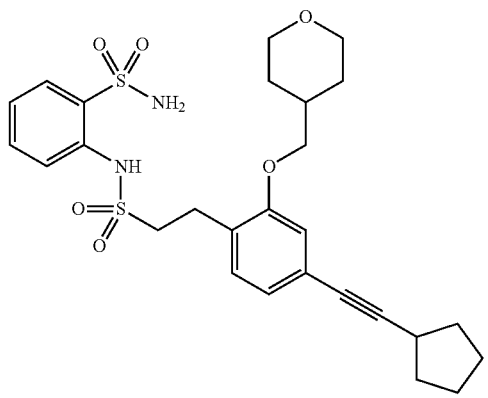 [SMILES: NS(=O)(=O)c1ccccc1NS(=O)(=O)CCc1ccc(C#CC2CCCC2)cc1OCC1CCOCC1]

The title compound was prepared following the procedure for Example 9 starting from 2-[({2-[4-bromo-2-(tetrahydro-2H-pyran-4-yl methoxy)phenyl]ethyl}sulfonyl)amino]benzenesulfonamide (160 mg, 0.3 mmol), copper(I) iodide (5.71 mg, 0.03 mmol), bis(triphenylphosphine)palladium(II)chloride (21.06 mg, 0.03 mmol) in DMF (3 mL), ethynylcyclopentane (0.10 mL, 0.90 mmol) and diisopropylamine (0.13 mL, 0.90 mmol). Purification by preparative HPLC gave 71 mg (43% yield) of the title compound. $^1$H NMR (500 MHz, DMSO-d$_6$) δ ppm 1.25 (qd, 2H), 1.49-1.77 (m, 8H), 1.81-2.04 (m, 3H), 2.79-2.89 (m, 1H), 2.93-3.02 (m, 2H), 3.28 (t, 2H), 3.42-3.51 (m, 2H), 3.79 (d, 2H), 3.84 (dd, 2H), 6.82-6.91 (m, 2H), 7.11 (d, 1H), 7.30-7.40 (m, 1H), 7.59-7.69 (m, 2H), 7.79-7.92 (m, 3H), 8.94 (s, 1H). MS (ES$^-$) m/z 545 [M−H]$^-$.

Example 12

2-[({2-[4-(cyclobutylethynyl)-2-(tetrahydro-2H-pyran-4-ylmethoxy)phenyl]ethyl}sulfonyl)amino]benzenesulfonamide

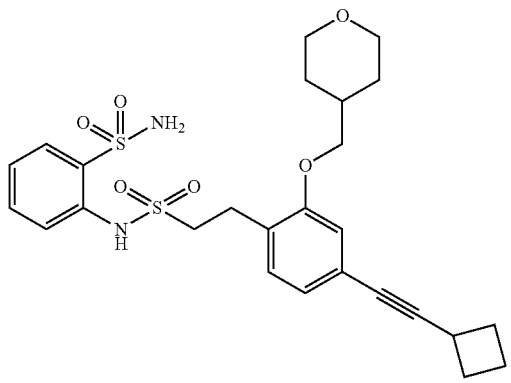 [SMILES: NS(=O)(=O)c1ccccc1NS(=O)(=O)CCc1ccc(C#CC2CCC2)cc1OCC1CCOCC1]

The title compound was prepared following the procedure for Example 9 starting from 2-[({2-[4-bromo-2-(tetrahydro-2H-pyran-4-ylmethoxy)phenyl]ethyl}sulfonyl)amino]benzenesulfonamide (250 mg, 0.47 mmol), (cyclobutylethynyl)trimethylsilane (107 mg, 0.70 mmol), copper(I)iodide (4.46 mg, 0.02 mmol), 1,1'-bis(diphenylphosphino)ferrocene-palladium(II)dichloride dichloromethane complex (19.14 mg, 0.02 mmol) and diisopropylamine (0.20 mL, 1.41 mmol). Purification by preparative HPLC gave 59 mg (24% yield) of the title compound. $^1$H NMR (500 MHz, CHLOROFORM-d) δ ppm 1.39-1.50 (m, 2H) 1.66-1.72 (m, 2H) 1.89-1.98 (m, 1H) 1.99-2.09 (m, 1H) 2.18-2.27 (m, 2H) 2.30-2.38 (m, 2H) 3.22 (d, J=8.51 Hz, 2H) 3.40 (d, J=1.58 Hz, 2H) 3.52 (s, 2H) 3.80 (d, J=5.99 Hz, 2H) 3.95-4.01 (m, 3H) 5.24 (s, 2H) 6.85 (d, J=0.95 Hz, 1H) 6.93-6.97 (m, 1H) 7.07 (s, 1H) 7.28-7.33 (m, 2H) 7.61 (d, J=1.58 Hz, 2H) 7.95-8.00 (m, 1H) 8.29 (s, 1H).

Example 13

2-[({2-[4-(3-methylbut-1-yn-1-yl)-2-(tetrahydro-2H-pyran-4-ylmethoxy)phenyl]ethyl}sulfonyl)amino]benzenesulfonamide

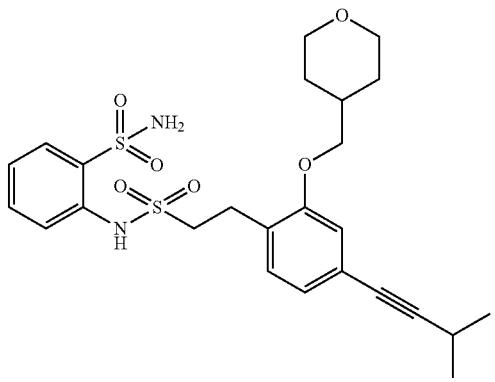 [SMILES: CC(C)C#Cc1ccc(CCS(=O)(=O)Nc2ccccc2S(N)(=O)=O)c(OCC2CCOCC2)c1]

The title compound was prepared following the procedure for Example 9, starting from 2-[({2-[4-bromo-2-(tetrahydro-2H-pyran-4-ylmethoxy)phenyl]ethyl}sulfonyl)amino]benzenesulfonamide (1.75 g, 3.27 mmol), 3-methyl-1-butyne (0.67 mL, 6.55 mmol), copper(I) iodide (0.031 g, 0.16 mmol), 1,1'-bis(diphenylphosphino)ferrocene-palladium dichloride (0.14 g, 0.16 mmol) and diisopropylamine (1.38 mL, 9.82 mmol) in N,N-dimethylformamide (12 mL). Purification by chromatography on silica using gradient elution 10-100% EtOAc in heptane followed by purification by preparative HPLC gave 0.41 g (24% yield) of the title compound. $^1$H NMR (400 MHz, DMSO-$d_6$) δ ppm 1.15-1.31 (m, 8H) 1.57 (m, 2H) 1.81-1.93 (m, 1H) 2.77 (m, 1H) 2.92-3.01 (m, 2H) 3.26 (m, 2H) 3.40-3.50 (m, 2H) 3.74-3.87 (m, 4H) 6.82-6.89 (m, 2H) 7.11 (d, 1H) 7.33 (t, 1H) 7.57-7.68 (m, 2H) 7.77-7.90 (m, 3H) 8.93 (s, 1H)). MS (ES⁻) m/z 519 [M−H]⁻.

Example 14

2-{[(2-{4-[(4-Methylphenyl)ethynyl]-2-(tetrahydro-2H-pyran-4-ylmethoxy)phenyl}ethyl) sulfonyl]amino}benzenesulfonamide

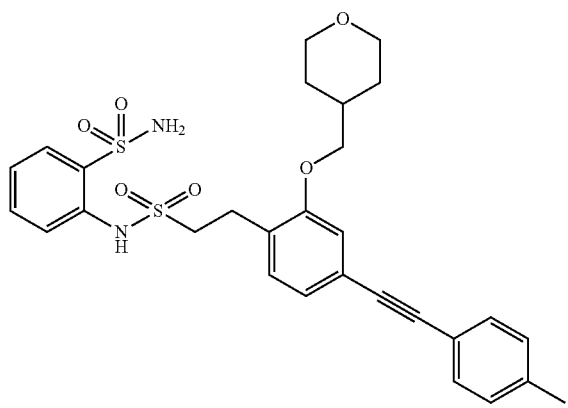 [SMILES: Cc1ccc(C#Cc2ccc(CCS(=O)(=O)Nc3ccccc3S(N)(=O)=O)c(OCC3CCOCC3)c2)cc1]

The title compound was prepared following the procedure for Example 9 starting from 2-[({2-[4-bromo-2-(tetrahydro-2H-pyran-4-ylmethoxy)phenyl]ethyl}sulfonyl)amino]benzenesulfonamide (200 mg, 0.37 mmol), 1-ethynyl-4-methylbenzene (65.3 mg, 0.56 mmol), copper(I) iodide (3.57 mg, 0.02 mmol), 1,1'-bis(diphenylphosphino)ferrocene-palladium(II)dichloride dichloromethane complex (15.31 mg, 0.02 mmol), and diisopropylamine (0.16 mL, 1.12 mmol) slurried in DMF (4 mL). Purification by preparative HPLC gave 100 mg (47% yield) of the title compound. $^1$H NMR (500 MHz, CHLOROFORM-d) δ ppm 1.46 (qd, J=12.40, 4.41 Hz, 2H) 1.70 (d, 1=11.66 Hz, 2H) 1.99-2.11 (m, 1H) 2.38 (s, 3H) 3.20-3.25 (m, 2H) 3.41 (t, J=11.19 Hz, 2H) 3.52-3.57 (m, 2H) 3.83 (d, J=6.31 Hz, 2H) 3.98 (dd, J=11.19, 3.63 Hz, 2H) 6.97 (s, 1H) 7.07 (dd, 1=7.72, 0.79 Hz, 1H) 7.12-7.18 (m, 3H) 7.27-7.31 (m, 1H) 7.42 (d, J=8.20 Hz, 2H) 7.56-7.61 (m, 1H) 7.63-7.66 (m, 1H) 7.98 (d, J=7.88 Hz, 1H) 8.36 (s, 1H)). MS (ES⁻) m/z 567 [M−H]⁻.

Example 15

2-[({2-[4-(3,3-Dimethylbut-1-yn-1-yl)-2-(tetrahydro-2H-pyran-4-ylmethoxy)phenyl]ethyl}sulfonyl)amino]benzenesulfonamide

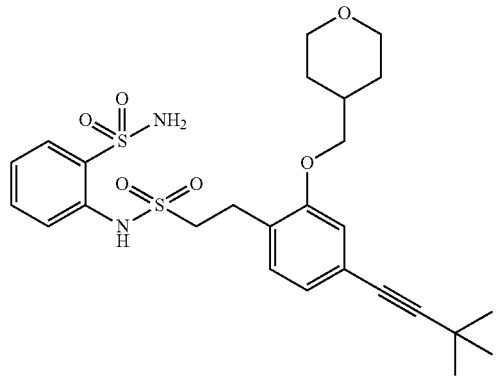 [SMILES: CC(C)(C)C#Cc1ccc(CCS(=O)(=O)Nc2ccccc2S(N)(=O)=O)c(OCC2CCOCC2)c1]

The title compound was prepared following the procedure for Example 9, starting from 2-[({2-[4-bromo-2-(tetrahydro-2H-pyran-4-ylmethoxy)phenyl]ethyl}sulfonyl)amino]benzenesulfonamide (100 mg, 0.19 mmol), copper(i) iodide (1.785 mg, 9.37 μmol), 1,1'-bis(diphenylphosphino)ferrocene-palladium(ii)dichloride dichloromethane complex (7.65 mg, 9.37 μmol), and diisopropylamine (0.08 mL, 0.56 mmol) in DMF (4 mL). Purification by preparative HPLC gave 69 mg (69% yield) of the title compound. $^1$H NMR (400 MHz, CHLOROFORM-d) δ ppm 1.31 (s, 9H) 1.37-1.51 (m, 2H) 1.67 (d, J=1.77 Hz, 2H) 1.96-2.11 (m, 1H) 3.17-3.24 (m, 2H) 3.40 (d, J=1.77 Hz, 2H) 3.49-3.55 (m, 2H) 3.81 (d, J=6.06 Hz, 2H) 3.94-4.01 (m, 2H) 6.83 (d, J=1.26 Hz, 1H) 6.92-6.96 (m, 1H) 7.07 (d, J=7.83 Hz, 1H) 7.27-7.32 (m, 1H) 7.60 (m, J=1.77 Hz, 1H) 7.98 (dd, J=7.96, 0.88 Hz, 1H) 8.30 (s, 1H). MS (ES⁻) m/z 533 [M−H]⁻

Intermediate 37

3-(Benzylsulfanyl)-4-nitrophenyl]methanol

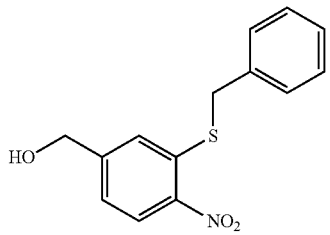 [SMILES: O=[N+]([O-])c1ccc(CO)cc1SCc1ccccc1]

Diisopropylethylamine (72 mL, 584 mmol) and benzyl mercaptan (39.87 g, 321 mmol) were added to a stirred solution of (3-fluoro-4-nitrophenyl)methanol (50 g, 292 mmol) in DMSO (250 mL). The reaction mixture was heated at 80° C. for 3 h, then cooled to room temperature, and poured into ice-water. The precipitated solid was collected by filtration, washed with water and dried under reduced pressure to give 87 g of the title compound that was used in the next step without further purification. $^1$H NMR (400 MHz, CHLOROFORM-d) δ ppm 4.20 (s, 2H) 4.73 (d, J=4.8 Hz, 2H) 7.30 (m, 4H) 7.43 (m, 2H) 7.53 (d, J=8 Hz, 1H) 8.21 (s, 1H).

Intermediate 38

{[3-(Benzylsulfanyl)-4-nitrobenzyl]oxy}(tert-butyl)diphenylsilane

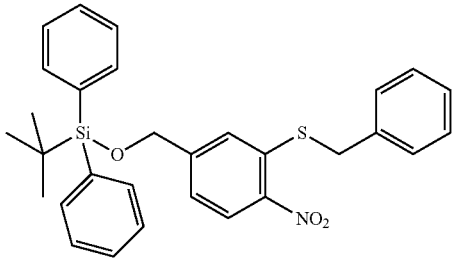 [SMILES: CC(C)(C)[Si](OCc1ccc([N+](=O)[O-])c(SCc2ccccc2)c1)(c1ccccc1)c1ccccc1]

A mixture of [3-(benzylsulfanyl)-4-nitrophenyl]methanol (87 g, 316 mmol), tert-butyldiphenylchlorosilane (86.86 g, 316 mmol) and imidazole (43.03 g, 632 mmol) in dry DMF (550 mL) was stirred at room temperature overnight. The reaction mixture was partitioned between water (0.5 L) and ethyl acetate (2 L). The organic phase was separated, washed with brine (3×0.5 L), dried over anhydrous sodium sulfate and concentrated under reduced pressure. Purification by chromatography on silica using gradient elution 5-10% EtOAc in heptane gave 148 g (99% yield) of the title compound. $^1$H NMR (400 MHz, CHLOROFORM-d) δ ppm 1.10 (s, 9H) 4.20 (s, 2H) 4.74 (s, 2H) 7.29-7.48 (m, 13H) 7.65 (d, J=8 Hz, 4H) 8.13 (s, 1H).

Intermediate 39

5-({[tert-Butyl(diphenyl)silyl]oxy}methyl)-2-nitrobenzenesulfonyl chloride

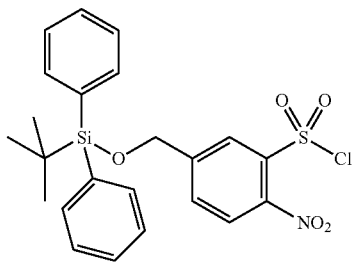 [SMILES: CC(C)(C)[Si](OCc1ccc([N+](=O)[O-])c(S(=O)(=O)Cl)c1)(c1ccccc1)c1ccccc1]

To a stirred solution of {[3-(benzylsulfanyl)-4-nitrobenzyl]oxy}(tert-butyl)diphenylsilane (10 g, 19.67 mmol) in dichloromethane (600 mL) were added formic acid (300 mL) and a solution of sodium chloride (18 g, 305.58 mmol) in water (300 mL). N-Chlorosuccinimide (24 g, 179.07 mmol) was then added in portions and the resulting mixture was stirred vigorously for about 1 h until all starting material was consumed. The organic phase was separated, dried over anhydrous sodium sulfate and concentrated under reduced pressure to give 10.2 g of the title compound, which was used in the next step without further purification. $^1$H NMR (400 MHz, CHLOROFORM-d) δ ppm 1.12 (s, 9H) 4.87 (s, 2H) 7.43 (m, 6H) 7.64 (d, J=8 Hz, 4H) 7.74 (d, J=8 Hz, 1H) 7.81 (s, 1H) 8.18 (d, J=8 Hz, 1H).

Intermediate 40

N-(tert-Butyl)-5-(((tert-butyldiphenylsilyl)oxy)methyl)-2-nitrobenzenesulfonamide

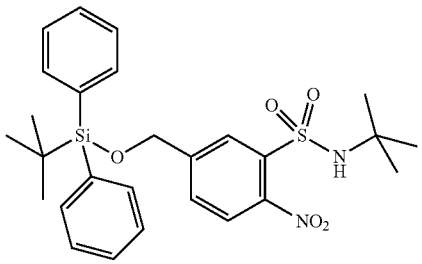 [SMILES: CC(C)(C)NS(=O)(=O)c1cc(CO[Si](c2ccccc2)(c2ccccc2)C(C)(C)C)ccc1[N+](=O)[O-]]

tert-Butylamine (36.5 mL, 346 mmol) was added dropwise to a stirred solution of 5-({[tert-butyl(diphenyl)silyl]oxy}methyl)-2-nitrobenzenesulfonyl chloride (36.5 g, crude) in methylenechloride (300 mL) at room temperature. The resulting mixture was stirred overnight and water (250 mL) was added. The organic layer was separated, dried over anhydrous sodium sulfate and concentrated under reduced pressure. Purification by chromatography on silica using gradient elution 4-12% EtOAc in heptane gave 18.9 g (48% yield, calculated over two steps from Intermediate 38) of the title compound. $^1$H NMR (400 MHz, Methanol-d$_4$) δ ppm 1.10 (s, 9H) 4.90 (s, 2H) 7.42 (m, 6H) 7.66 (d, J=8 Hz, 4H) 7.74 (d, J=8 Hz, 1H) 7.80 (s, 1H) 8.05 (d, J=8 Hz, 1H).

Intermediate 41

2-Amino-N-tert-butyl-5-({[tert-butyl(di phenyl)silyl]oxy}methyl)benzenesulfonamide

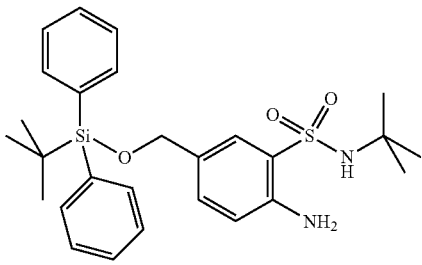 [SMILES: CC(C)(C)NS(=O)(=O)c1cc(CO[Si](c2ccccc2)(c2ccccc2)C(C)(C)C)ccc1N]

To a stirred solution of N-(tert-butyl)-5-(((tert-butyldiphenylsilyl)oxy)methyl)-2-nitrobenzenesulfonamide (4.61 g, 8.75 mmol) was added ammonium chloride (2.34 g, 43.75 mmol) followed by zinc dust (4.61 g, 96 mmol). The reaction mixture was heated to reflux for 2 h, then cooled to room temperature and filtered through a pad of Celite. The filtrate was concentrated under reduced pressure and the residue was partitioned between dichloromethane (100 mL) and water (50 mL). The organic layer was separated, washed with brine (50 mL), dried over anhydrous sodium sulfate and concentrated under reduce pressure to give 4.3 g (99% yield) of the title compound. $^1$H NMR (400 MHz, CHLOROFORM-d) δ ppm 1.07 (s, 9H) 1.19 (s, 9H) 4.65 (s, 2H) 4.69 (s, 1H) 4.74 (s, 2H) 6.71 (d, J=8.00 Hz, 1H) 7.26 (dd, J=8.00, 2.00 Hz, 1H) 7.39 (m, 6H) 7.67 (m, 4H) 7.73 (d, J=2.00 Hz, 1H). MS (ES$^+$) m/z: [M+1]$^+$497.11.

Intermediate 42

2-[Bis(methylsulfonyl)amino]-N-tert-butyl-5-({[tert-butyl(diphenyl)silyl]oxy}methyl)benzenesulfonamide

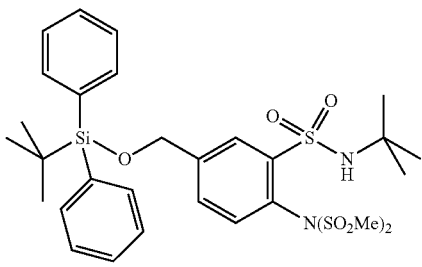

Methanesulfonyl chloride (27.6 g, 241 mmol) was added dropwise to a stirred mixture of 2-amino-N-tert-butyl-5-({[tert-butyl(diphenyl)silyl]oxy}methyl)benzenesulfonamide (57 g, 115 mmol) and triethylamine (24.4 g, 241 mmol) in methylenechloride (200 mL) at 0° C. The reaction mixture was stirred at 0° C. for 0.5 h and then at room temperature for 1 h. The reaction mixture was diluted with methylenechloride (700 mL), washed with water (500 mL), saturated sodium bicarbonate (500 mL) and brine (500 mL). The organic layer was separated, dried over anhydrous sodium sulfate and concentrated under reduced pressure to give 74.9 g (100% yield) of the title compound. $^1$H NMR (400 MHz, CHLOROFORM-d) δ ppm 1.12 (s, 9H) 1.31 (s, 9H) 3.57 (s, 6H) 4.82 (s, 2H) 5.22 (s, 1H) 7.39 (m, 7H) 7.60 (d, 1H) 7.67 (d, 4H) 8.23 (d, J=2.00 Hz, 1H).

Intermediate 43

N-tert-Butyl-5-({[tert-butyl(diphenyl)silyl]oxy}methyl)-2-[(methylsulfonyl)amino]benzenesulfonamide

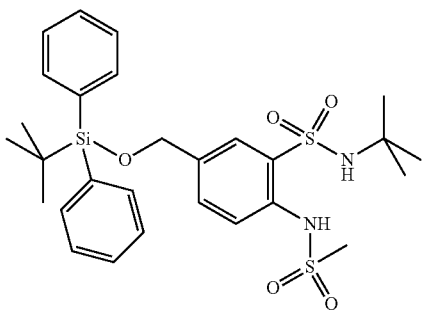 [SMILES: CC(C)(C)NS(=O)(=O)c1cc(CO[Si](c2ccccc2)(c2ccccc2)C(C)(C)C)ccc1NS(C)(=O)=O]

Aqueous NaOH (2 M, 173 mL, 345 mmol) was added to a stirred solution of 2-[bis(methylsulfonyl)amino]-N-tert-butyl-5-({[tert-butyl(di phenyl)silyl]oxy}methyl)benzenesulfonamide (74.92 g, 115 mmol) in THF (270 mL) at room temperature. The resulting mixture was stirred for 2 h, neutralized using hydrochloric acid (2 M) and extracted with methylenechloride (2×500 mL). The combined extracts were washed with water (500 mL) and brine (500 mL), dried over anhydrous sodium sulfate and concentrated under reduced pressure to give 58 g (88% yield) of the title compound. $^1$H NMR (400 MHz, CHLOROFORM-d) δ ppm 1.10 (s, 9H) 1.23 (s, 9H) 3.16 (s, 3H) 4.75 (s, 2H) 4.99 (s, 1H) 7.63 (m, 5H) 7.43 (m, 7H) 7.97 (d, J=2.00 Hz, 1H) 8.29 (s, 1H). MS (ES$^-$) m/z: 573.29[M−1]$^-$

Intermediate 44

N-tert-Butyl-2-({[2-(2-{[tert-butyl(dimethyl)silyl]oxy}-4-chlorophenyl)ethyl]sulfonyl}amino)-5-({[tert-butyl(diphenyl)silyl]oxy}methyl)benzenesulfonamide

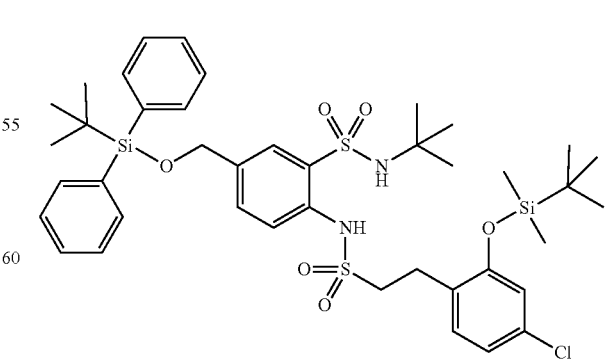

A solution of N-tert-butyl-5-({[tert-butyl(diphenyl)silyl]oxy}methyl)-2-[(methyl-sulfonyl)amino]benzenesulfonamide (7.70 g, 13.40 mmol) was treated at −78° C. with lithium diisopropylamide (21.45 mL, 42.89 mmol). After 10 minutes, a solution of [2-(bromomethyl)-5-chlorophenoxy](tert-butyl)dimethylsilane (4.5 g, 13.40 mmol) in THF (15 mL) was added dropwise under 50 min. The reaction mixture was stirred at −78° C. for 1.5 h then allowed to reach room temperature and stirred for another 1.5 h. The reaction mixture was quenched with brine and extracted with ethyl acetate. The organic layer was washed with brine, dried over magnesium sulfate, filtered and concentrated under reduced pressure. Purification by chromatography on silica using gradient elution 12-20% EtOAc in heptane gave 6.55 g (59% yield) of the title compound. $^1$H NMR (500 MHz, DMSO-$d_6$) δ ppm 0.17 (s, 6H) 0.87 (s, 9H) 1.00-1.05 (m, 9H) 1.07 (s, 9H) 2.93-3.05 (m, 2H) 3.40-3.52 (m, 2H) 4.79 (s, 2H), 6.78 (d, 1H) 6.96 (dd, 1H) 7.20 (d, 1H) 7.37-7.44 (m, 4H) 7.44-7.49 (m, 2H) 7.51 (dd, 1H) 7.60-7.68 (m, 5H) 7.98 (s, 1H) 8.01 (s, 1H) 8.73 (s, 1H).

Intermediate 45

N-tert-Butyl-2-({[2-(2-{[tert-butyl(dimethyl)silyl]oxy}-4-fluorophenyl)ethyl]sulfonyl}amino)-5-({[tert-butyl(diphenyl)silyl]oxy}methyl)benzenesulfonamide

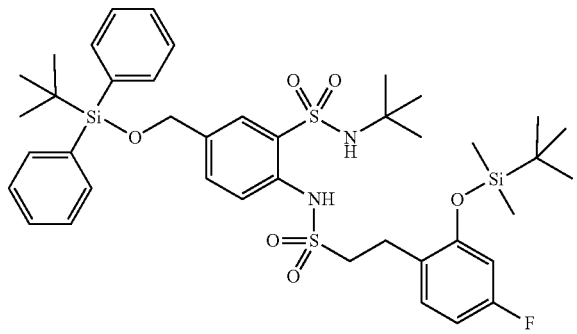 [SMILES: CC(C)(C)NS(=O)(=O)c1cc(CO[Si](c2ccccc2)(c2ccccc2)C(C)(C)C)ccc1NS(=O)(=O)CCc1ccc(F)cc1O[Si](C)(C)C(C)(C)C]

A solution of N-tert-butyl-5-({[tert-butyl(diphenyl)silyl]oxy}methyl)-2-[(methylsulfonyl)amino]benzenesulfonamide (0.985 g, 1.71 mmol) in tetrahydrofuran (25 mL) was treated at −78° C. with lithium diisopropylamide (2.74 mL, 5.48 mmol). After 10 minutes, a solution of [2-(bromomethyl)-5-fluorophenoxy](tert-butyl)dimethylsilane (0.55 g, 1.71 mmol) in THF (15 mL) was added dropwise under 5 min. The reaction mixture was stirred at −78° C., for 90 min and was then allowed to reach room temperature and was stirred for another 60 min. The reaction mixture was quenched with brine and ethyl acetate was added. The phases were separated and the organic layer was washed with brine, dried over magnesium sulfate, filtered and concentrated under reduced pressure. Purification by chromatography on silica using gradient elution 0-50% EtOAc in heptane gave 0.59 g (42% yield) of the title compound, which was used directly in the next step without further purification.

Intermediate 46

N-tert-Butyl-5-({[tert-butyl(diphenyl)silyl]oxy}methyl)-2-({[2-(4-chloro-2-hydroxyphenyl)ethyl]sulfonyl}amino)benzenesulfonamide

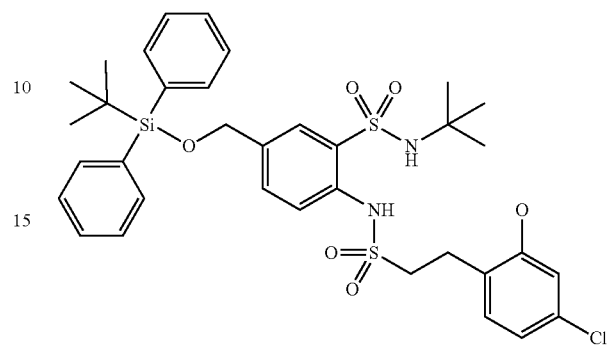

To a cold (0° C.) solution of N-tert-butyl-2-({[2-(2-{[tert-butyl(dimethyl)silyl]oxy}-4-chloro-phenyl)ethyl]sulfonyl}amino)-5-({[tert-butyl(diphenyl)silyl]oxy}methyl)benzenesulfonamide (6.55 g, 7.89 mmol) in THF (60 mL) tetrabutylammonium fluoride (4.25 mL, 11.84 mmol) was added. The reaction mixture was allowed to reach room temperature and stirred for 1.5 h. Additional tetrabutylammonium fluoride (4.14 mL, 11.84 mmol) was added and more tetrabutylammonium fluoride (4.14 mL, 11.84 mmol) was added after 30 min followed by stirring for another 30 min. The reaction mixture was quenched by addition of saturated brine, extracted with ethylacetate, the organic layer was washed with a saturated NH$_4$Cl(aq) solution, dried over magnesium sulfate, filtered and concentrated under reduced pressure. Purification by chromatography on silica using gradient elution 25-50% EtOAc in heptane followed by EtOAc 100% gave 5.6 g (99% yield) of the title compound. $^1$H NMR (500 MHz, DMSO-$d_6$) δ ppm 1.03 (s, 9H) 1.09 (s, 9H) 2.88-2.99 (m, 2H) 3.42-3.55 (m, 2H) 4.79 (s, 2H) 6.70-6.81 (m, 2H) 7.08 (d, 1H) 7.38-7.44 (m, 4H) 7.44-7.54 (m, 3H) 7.59-7.69 (m, 5H) 8.01 (d, 2H) 8.74 (s, 1H) 10.06 (s, 1H). MS (ES$^-$) m/z 713, 715, 717 [M−H]$^-$.

Intermediate 47

N-tert-Butyl-5-({[tert-butyl(diphenyl)silyl]oxy}methyl)-2-({[2-(4-fluoro-2-hydroxyphenyl)ethyl]sulfonyl}amino)benzenesulfonamide

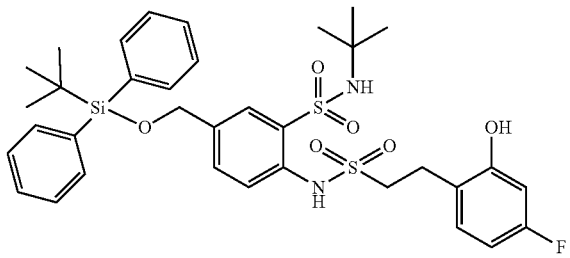 [SMILES: CC(C)(C)NS(=O)(=O)c1cc(CO[Si](c2ccccc2)(c2ccccc2)C(C)(C)C)ccc1NS(=O)(=O)CCc1ccc(F)cc1O]

To a cold (0° C.) solution of N-tert-butyl-2-({[2-(2-{[tert-butyl(dimethyl)silyl]oxy}-4-fluorophenyl)ethyl]sulfonyl}amino)-5-({[tert-butyl(diphenyl)silyl]oxy}methyl)benzenesulfonamide (59 mg, 0.72 mmol) in THF (15 mL) was tetrabutylammonium fluoride (0.87 mL, 0.87 mmol) added. The reaction mixture was stirred for 3 h, the reaction mixture was quenched by addition of saturated brine solution, extracted with ethylacetate, the organic layer was washed with saturated NH$_4$Cl(aq), dried over magnesium sulfate, filtered and concentrated, to give 392 mg (78% yield) of the title compound. MS (ES⁻) m/z 697 [M−H]⁻.

Intermediate 48

N-tert-Butyl-5-({[tert-butyl(diphenyl)silyl] oxy}methyl)-2-[({2-[4-chloro-2-(tetrahydro-2H-pyran-4-yl methoxy)phenyl]ethyl}sulfonyl)amino] benzenesulfonamide

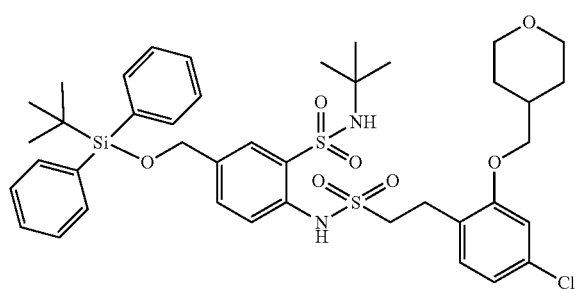 [SMILES: CC(C)(C)NS(=O)(=O)c1cc(CO[Si](c2ccccc2)(c2ccccc2)C(C)(C)C)ccc1NS(=O)(=O)CCc1ccc(Cl)cc1OCC1CCOCC1]

N-tert-Butyl-5-({[tert-butyl(diphenyl)silyl]oxy}methyl)-2-({[2-(4-chloro-2-hydroxyphenyl)ethyl]sulfonyl}amino) benzenesulfonamide (4.05 g, 5.67 mmol) divided in three vials (1.35 g, 1.89 mmol in each vial), cesium carbonate (2.77 g, 8.49 mmol in each vial), 4-bromomethyltetrahydropyran (1.52 g, 8.49 mmol in each vial) and N,N-dimethylformamide (12 mL in each vial) were mixed and heated in a MW at 110° C. for 1 h. The reaction mixtures were filtered and the solvent was evaporated. The combined crude product was mixed with water/ethyl acetate and the aqueous phase was extracted twice with ethyl acetate. The combined organic extracts were washed with brine, dried over magnesium sulfate, filtered and the solvent was evaporated. Purification by chromatography on silica using gradient elution 5-50% EtOAc in heptane gave 3.23 g (70% yield) of the title compound. ¹H NMR (500 MHz, DMSO-d₆) δ ppm 1.04 (s, 9H) 1.08 (s, 9H) 1.11 (s, 1H) 1.18-1.28 (m, 2H) 1.52-1.58 (m, 2H) 1.83-1.91 (m, 1H) 2.94-2.99 (m, 2H) 3.20-3.27 (m, 2H) 3.44-3.49 (m, 2H) 3.79 (m, 3H) 4.79 (s, 2H) 6.91 (dd, 1H) 7.01 (d, 1H) 7.18 (d, 1H) 7.40-7.45 (m, 4H) 7.46 (d, 2H) 7.52 (dd, 1H) 7.61-7.65 (m, 5H) 7.99 (s, 1H) 8.03 (d, 1H) 8.73 (s, 1H). MS (ES⁻) m/z 811, 813 [M−H]⁻.

Intermediate 49

N-tert-Butyl-5-({[tert-butyl(di phenyl)silyl] oxy}methyl)-2-[({2-[4-fluoro-2-(tetrahydro-2H-pyran-4-yl methoxy)phenyl]ethyl}sulfonyl)amino] benzenesulfonamide

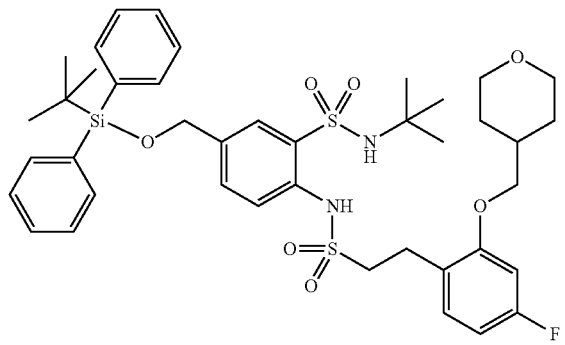 [SMILES: CC(C)(C)NS(=O)(=O)c1cc(CO[Si](c2ccccc2)(c2ccccc2)C(C)(C)C)ccc1NS(=O)(=O)CCc1ccc(F)cc1OCC1CCOCC1]

N-tert-Butyl-5-({[tert-butyl(diphenyl)silyl]oxy}methyl)-2-({[2-(4-fluoro-2-hydroxyphenyl)ethyl]-sulfonyl}amino) benzenesulfonamide (392 mg, 0.56 mmol) and 4-(bromomethyl)tetrahydro-2H-pyran (502 mg, 2.80 mmol) were added to a solution of cesium carbonate (914 mg, 2.80 mmol) in DMF (3 mL), the reaction mixture was heated in a MW at 110° C. for 2 h. The mixture was filtered through a plug of celite and concentrated. Purification by chromatography on silica using gradient elution 0-50% EtOAc in heptane gave 0.24 g (54% yield) of the title compound. MS (ES⁻) m/z 795, 796, 797 [M−H]⁻.

Intermediate 50

N-tert-Butyl-2-[({2-[4-chloro-2-(tetrahydro-2H-pyran-4-yl methoxy)phenyl]ethyl}sulfonyl)amino]-5-(hydroxymethyl)benzenesulfonamide

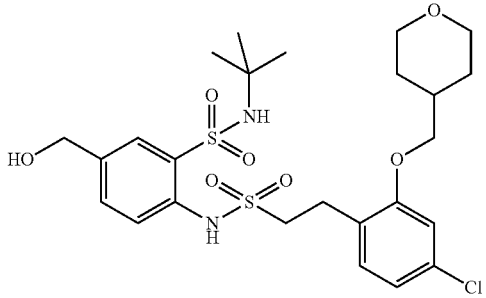 [SMILES: CC(C)(C)NS(=O)(=O)c1cc(CO)ccc1NS(=O)(=O)CCc1ccc(Cl)cc1OCC1CCOCC1]

To N-tert-butyl-5-({[tert-butyl(diphenyl)silyl] oxy}methyl)-2-[({2-[4-chloro-2-(tetrahydro-2H-pyran-4-yl-methoxy)phenyl]ethyl}sulfonyl)amino]benzenesulfonamide (3.23 g, 3.97 mmol) dissolved in anhydrous tetrahydrofuran (60 mL) tetrabutylammonium fluoride (1M in THF) (15.88 mL, 15.88 mmol) was added. The mixture was stirred at room temperature over night. The solvent was evaporated and the crude product was dissolved in ethyl acetate. The organic phase was washed with water, brine, dried over magnesium sulfate, filtered and the solvent was evaporated. Purification by chromatography on silica using gradient elution 5-100% EtOAc in heptane, yielded the title compound (1.876 g, 82%). ¹H NMR (500 MHz, DMSO-d₆) δ ppm 1.08 (s, 9H) 1.19-1.29 (m, 2H) 1.53-1.60 (m, 2H) 1.83-1.93 (m, 1H) 2.96 (m, 2H) 3.26 (m, 2H) 3.45 (m, 2H) 3.81 (m, 4H) 4.51 (d, 2H) 5.41 (t, 1H) 6.91 (dd, 1H) 7.00 (d, 1H) 7.17 (d, 1H) 7.53 (m, 1H) 7.62 (m, 1H) 7.87 (d, 1H) 7.96 (s, 1H) 8.72 (s, 1H); MS (ES⁻) m/z 573, 575, [M−H]⁻.

Intermediate 51

N-tert-butyl-2-[({2-[4-fluoro-2-(tetrahydro-2H-pyran-4-ylmethoxy)phenyl]ethyl}sulfonyl)amino]-5-(hydroxymethyl)benzenesulfonamide

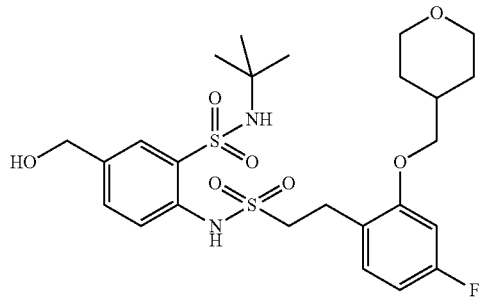 [SMILES: CC(C)(C)NS(=O)(=O)c1cc(CO)ccc1NS(=O)(=O)CCc1ccc(F)cc1OCC1CCOCC1]

To a solution of N-tert-butyl-5-({[tert-butyl(diphenyl)silyl]oxy}methyl)-2-[({2-[4-fluoro-2-(tetrahydro-2H-pyran-4-ylmethoxy)phenyl]ethyl}sulfonyl)amino]benzenesulfonamide (242 mg, 0.30 mmol) in THF (5 mL) at 0° C. a solution of tetrabutylammonium fluoride (1.0 M solution in THF) (1.822 mL, 1.82 mmol) was slowly added. The reaction mixture was stirred over night at r.t. The reaction mixture was quenched by addition of sat. brine solution extracted with ethylacetate, the organic layer was washed with sat. aq. NH4Cl, dried over magnesium sulfate, filtered and concentrated. The product was used in the next step without further purification.

Example 16

2-[({2-[4-chloro-2-(tetrahydro-2H-pyran-4-yl-methoxy)phenyl]ethyl}sulfonyl)amino]-5-(hydroxymethyl)benzenesulfonamide

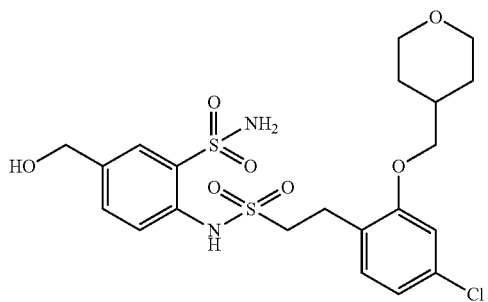 [SMILES: NS(=O)(=O)c1cc(CO)ccc1NS(=O)(=O)CCc1ccc(Cl)cc1OCC1CCOCC1]

Tetrabutylammonium fluoride (1.0 M solution in THF) (1.490 mL, 1.49 mmol) was added slowly to a solution of N-tert-butyl-5-({[tert-butyl(diphenyl)silyl]oxy}methyl)-2-[({2-[4-chloro-2-(tetrahydro-2H-pyran-4-ylmethoxy)phenyl]ethyl}sulfonyl)amino]benzenesulfonamide (202 mg, 0.25 mmol) in THF (5 mL) at 0° C. The reaction mixture was stirred over night at room temperature. The reaction mixture was quenched by addition of sat. aq brine solution and extracted with ethylacetate. The organic phase was washed with sat. aq. NH4Cl, dried over magnesium sulfate, filtered and concentrated. The residue was dissolved in 2 ml of TFA 12:39:39 and was stirred for 1.5 hours. Purification by preparative HPLC gave the title compound (0.039 g, 30%). $^1$H NMR (500 MHz, METHANOL-$d_4$) δ ppm 1.34-1.44 (m, 2H) 1.67-1.74 (m, 2H) 1.97-2.06 (m, 1H) 3.03-3.09 (m, 2H) 3.44 (br. s., 4H) 3.78 (s, 2H) 3.92-3.99 (m, 2H) 4.63 (s, 2H) 6.82-6.86 (m, 1H) 6.89-6.94 (m, 1H) 7.08-7.12 (m, 1H) 7.54-7.58 (m, 1H) 7.70-7.74 (m, 1H) 7.94-7.98 (m, 1H); MS (ES$^-$) m/z 517, 519 [M−H]$^-$.

Example 17

2-[({2-[4-fluoro-2-(tetrahydro-2H-pyran-4-yl-methoxy)phenyl]ethyl}sulfonyl)amino]-5-(hydroxymethyl)benzenesulfonamide

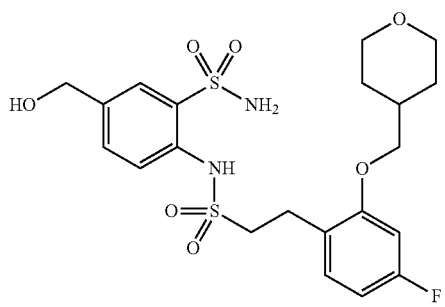 [SMILES: NS(=O)(=O)c1cc(CO)ccc1NS(=O)(=O)CCc1ccc(F)cc1OCC1CCOCC1]

N-tert-butyl-5-({[tert-butyl(di phenyl)silyl]oxy}methyl)-2-[({2-[4-fluoro-2-(tetrahydro-2H-pyran-4-ylmethoxy)phenyl]ethyl}sulfonyl)amino]benzenesulfonamide (0.242 g, 0.30 mmol) in THF (5 mL) at 0° C. a solution of Tetrabutylammonium fluoride (1.0 M solution in THF) (1.822 mL, 1.82 mmol) was slowly added. The reaction mixture was stirred over night at room temperature. The reaction mixture was quenched by addition of brine solution and extracted with ethylacetate, the organic layer was washed with sat. aq. NH4Cl, dried over magnesium sulfate. The solvent was removed under reduced pressure. The remaining solid was dissolved in 2 ml of TFA 12:39:39 and stirred for 1.5 hours. Purification was done in several steps. Purification by preparative HPLC under acidic conditions. Followed by chromatography on silica using gradient elution 0-50% EtOAc in Heptane) and 0-10% MeOH/CHCl3. Final purification by yielded the title compound (0.017 g, 11%). $^1$H NMR (500 MHz, METHANOL-$d_4$) δ ppm 1.34-1.41 (m, 2H) 1.37-1.37 (m, 0H) 1.70 (dd, J=12.93, 1.89 Hz, 2H) 2.01 (br. s., 1H) 3.01-3.08 (m, 2H) 3.40-3.48 (m, 4H) 3.77 (d, J=6.62 Hz, 2H) 3.95 (dd, J=11.03, 3.47 Hz, 2H) 4.63 (s, 2H) 6.55 (td, J=8.35, 2.52 Hz, 1H) 6.68 (dd, J=11.19, 2.36 Hz, 1H) 7.10 (dd, J=8.35, 6.78 Hz, 1H) 7.55 (dd, J=8.35, 2.05 Hz, H) 7.72 (d, J=8.51 Hz, 1H) 7.96 (d, J=1.89 Hz, 1H); MS (ES$^-$) m/z 501 [M−H]$^-$.

Biological Assays
Assays for Determining Biological Activity
Inhibition of Prostaglandin E Synthase Activity Compounds were tested as inhibitors of microsomal prostaglandin E synthase activity in microsomal prostaglandin E synthase assays and whole cell assays. These assays measure prostaglandin E2 (PGE2) synthesis, which is taken as a measure of prostaglandin E synthase activity. Microsomal prostaglandin E synthase biochemical assays used microsomal prostaglandin E synthase-1 in microsomal preparations. The source of the microsomes can be for example interleukin-1β-stimulated human A549 cells (which express human mPGES-1) or Sf9 cells transfected with plasmids encoding human mPGES-1 cDNA.

The whole blood assay [described by Patrignani, P. et al, Journal of Pharmacology and Experimental Therapeutics, 1994, vol. 271, pp 1705-1712] was used as the whole cell assay for testing the compounds. Whole blood provides a protein and cell rich environment for the study of biochemical efficacy of anti-inflammatory compounds, such as prostaglandin synthase inhibitors. To study the inhibitory activities of these compounds, human blood was stimulated with lipopolysaccharide (LPS) for typically 16 hours to induce mPGES-1 expression, after which the concentration of produced PGE2 was measured by competitive-immuno assay (homogeneous time-resolved fluorescence, HTRF) as read out for effectiveness against mPGES-1-dependent PGE2 production.

Microsomal Prostaglandin E Synthase Biochemical Assay

A solution of test compound was added to a diluted microsome preparation containing human mPGES-1 and pre-incubated for 15 minutes in potassium phosphate buffer pH 6.8 with cofactor glutathione (GSH). Corresponding solutions without test compound were used as positive controls, and corresponding solutions without test compound and without microsomes were used as negative controls. The enzymatic reaction was then started by addition of the substrate PGH2 in an organic solution (dry acetonitrile).

The typical reaction conditions of the enzymatic reaction were thus: Test compound: ranging from 60 μM to 0.002 μM, or zero in positive and negative controls; potassium phosphate buffer pH 6.8:50 mM; GSH: 2.5 mM; mPGES-1-containing microsomes: 2 μg/mL (sample and positive controls) or 0 μg/mL (negative control); PGH2: 10.8 μM;

Acetonitrile: 7.7% (v/v); DMSO: 0.6% (v/v). The reaction was stopped after one minute by adding an acidic solution (pH 1.9) of ferric chloride and citrate (final concentrations 7 mM and 47 mM respectively), by which the PGH2 was sequestered (the PGH2 is reduced to mainly 12-hydroxy heptadecatrineoic acid (12-HHT) which is not detected by the subsequent PGE2 detection step). The resulting solution was then pH neutralized by addition of potassium phosphate buffer, prior to diluting an aliquot of the resulting solution in a weak potassium phosphate buffer (50 mM, pH 6.8) containing 0.2% BSA (w/v). [Adapted from Jacobsson et al., Proc. Natl. Acad. Sci. USA, 1999, vol. 96, pp. 7220-7225] The PGE2 formed was quantified by use of a commercial HTRF based kit (catalogue #62PG2PEC or #62P2APEC from Cisbio International). 100% activity was defined as the PGE2 production in positive controls subtracted by the PGE2 production in the negative controls. IC50 values were then determined using standard procedures.

Data from this assay for representative compounds is shown in the Table below. The potency is expressed as IC50 and the value indicated is an average of at least n=2. The data indicate that the compounds of the invention are expected to possess useful therapeutic properties.

Results

| Example | mPGES-1 (nM) | hWBA (nM) |
|---|---|---|
| 1 | 3.4 | 63.9 |
| 2 | 3.5 | 24.9 |
| 3 | 4.0 | 26.6 |
| 4 | 15 | 154 |
| 5 | 16 | 89.7 |
| 6 | 2.7 | 11.5 |
| 7 | 7.2 | 54.1 |
| 8 | 7.6 | 149 |
| 9 | 3.4 | 0.911 |
| 10 | <2.2 | 7.92 |
| 11 | 2.1 | 0.987 |
| 12 | <2.3 | 1.84 |
| 13 | 3.4 | 1.85 |
| 14 | 2.1 | 0.987 |
| 15 | <2.5 | 17.1 |
| 16 | 5.6 | 29 |
| 17 | 19.5 | 214 |

Whole Blood Assay

Human blood collected from human volunteers in heparinized tubes was incubated with 100 μM acetyl salicylic acid, in order to inhibit the constitutively expressed cyclooxygenase (COX)-1/COX-2 enzymes, and then stimulated with 0.1 μg/ml LPS to induce the expression of enzymes along the COX-2 pathway, e.g. COX-2 and mPGES-1. 100 μL of this blood was added to the wells of a 384-well plate containing 1 μL DMSO solutions of compounds typically in the final concentration range 316 μM to 0.01 μM. Naproxen was used as reference compound. The mix was incubated at 37° C. for 16 hours. Plasma was harvested by centrifugation and stored at −70° C. until further analysis of PGE2 levels. For the calculations, the 0%-activity value was represented by blood treated with acetyl salicylic acid, LPS and the reference compound (1 mM Naproxen). The 100%-activity value was represented by blood treated with aspirin, LPS and DMSO. [Reference: Patrignani, P. et al, Journal of Pharmacology and Experimental Therapeutics, 1994, vol. 271, pp 1705-1712]. The PGE2 formed was quantified, after dilution in a weak potassium phosphate buffer (50 mM, pH 6.8) containing 0.2% BSA (w/v), by use of a commercial HTRF based kit (catalogue #62PG2PEC or #62P2APEC from Cisbio International). IC50 values were then determined using standard procedures.

The results show that the novel bis(sulfonamide) compounds are selective inhibitors of the microsomal prostaglandin E synthase-1 enzyme. The compounds have an improved potency and selectivity.

The invention claimed is:

1. A compound of formula (I), or a pharmaceutically acceptable salt thereof

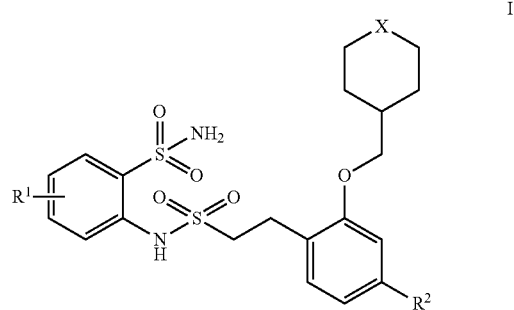

wherein:
$R^1$ is H or —CH$_2$OH;
$R^2$ is H, halogen, C$_{1-4}$-alkyl, fluoro-C$_{1-4}$-alkyl or —C≡C—R$^3$;
$R^3$ is H, C$_{1-4}$-alkyl, C$_{3-7}$-cycloalkyl or phenyl, wherein phenyl is optionally substituted with one or more substituents independently selected from C$_{1-4}$-alkyl, halogen, C$_{1-4}$-alkoxy and cyano;
X is CH$_2$, CHF, CF$_2$, O, S, SO, SO$_2$, NH or NR$^4$; and
$R^4$ is C$_{1-4}$alkyl.

2. The compound of formula (I) according to claim 1, wherein
$R^1$ is H or —CH$_2$OH;
$R^2$ is H, halogen, C$_{1-4}$-alkyl, fluoro-C$_{1-4}$-alkyl or —C≡C—R$^3$;
$R^3$ is C$_{1-4}$-alkyl, C$_{3-7}$-cycloalkyl or phenyl, wherein phenyl is optionally substituted with one or more C$_{1-4}$-alkyl;
X is CH$_2$, CHF, CF$_2$, O, S, SO, SO$_2$, NH or NR$^4$; and
$R^4$ is C$_{1-4}$alkyl.

3. The compound of formula (I) according to claim 1, wherein
$R^1$ is H or —CH$_2$OH;
$R^2$ is bromine, chlorine, fluorine, CH$_3$, CF$_3$ or —C≡C—R$^3$;
$R^3$ is C$_{1-4}$-alkyl, C$_{3-7}$-cycloalkyl or phenyl, wherein phenyl is optionally substituted with one or more C$_{1-4}$-alkyl; and
X is CH$_2$, CF$_2$ or O.

4. The compound of formula (I) according to claim 1, wherein
$R^1$ is H or —CH$_2$OH;
$R^2$ is bromine, chlorine, fluorine, CH$_3$, CF$_3$ or —C≡C—R$^3$;
$R^3$ is tert-butyl, iso-propyl, cyclobutyl, cyclopropyl, cyclopentyl, phenyl, wherein phenyl is optionally substituted with a CH$_3$ group; and
X is CF$_2$ or O.

5. The compound of formula (I) according to claim 1, wherein R$^1$ is —CH$_2$OH.

6. The compound of formula (I) according to claim 1, wherein $R^2$ is chlorine.

7. The compound of formula (I) according to claim 1, wherein X is O.

8. A compound, or a pharmaceutically acceptable salt thereof selected from the group consisting of
- 2-[({2-[4-Bromo-2-(tetrahydro-2H-pyran-4-ylmethoxy)phenyl]ethyl}sulfonyl)amino]benzenesulfonamide,
- 2-[({2-[4-Chloro-2-(tetrahydro-2H-pyran-4-ylmethoxy)phenyl]ethyl}sulfonyl)amino]benzenesulfonamide,
- 2-[({2-[2-(Tetrahydro-2H-pyran-4-ylmethoxy)-4-(trifluoromethyl)phenyl]ethyl}sulfonyl)amino]benzenesulfonamide,
- 2-[({2-[4-methyl-2-(tetrahydro-2H-pyran-4-ylmethoxy)phenyl]ethyl}sulfonyl)amino]benzenesulfonamide,
- 2-[({2-[4-Fluoro-2-(tetrahydro-2H-pyran-4-ylmethoxy)phenyl]ethyl}sulfonyl)amino]benzenesulfonamide,
- 2-{[(2-{4-Chloro-2-[(4,4-difluorocyclohexyl)methoxy]phenyl}ethyl)sulfonyl]amino}benzenesulfonamide,
- 2-{[(2-{2-[(4,4-Difluorocyclohexyl)methoxy]-4-methylphenyl}ethyl)sulfonyl]amino}benzenesulfonamide,
- 2-{[(2-{2-[(4,4-Difluorocyclohexyl)methoxy]-4-fluorophenyl}ethyl)sulfonyl]amino}benzenesulfonamide,
- 2-[({2-[4-(Phenylethynyl)-2-(tetrahydro-2H-pyran-4-ylmethoxy)phenyl]ethyl}sulfonyl)amino]benzenesulfonamide,
- 2-[({2-[4-(Cyclopentylethynyl)-2-(tetrahydro-2H-pyran-4-ylmethoxy)phenyl]ethyl}sulfonyl)amino]benzenesulfonamide,
- 2-[({2-[4-(Cyclopropylethynyl)-2-(tetrahydro-2H-pyran-4-ylmethoxy)phenyl]ethyl}sulfonyl)amino]benzenesulfonamide,
- 2-[({2-[4-(cyclobutylethynyl)-2-(tetrahydro-2H-pyran-4-ylmethoxy)phenyl]ethyl}sulfonyl)amino]benzenesulfonamide,
- 2-[({2-[4-(3-methylbut-1-yn-1-yl)-2-(tetrahydro-2H-pyran-4-ylmethoxy)phenyl]ethyl}sulfonyl)amino]benzenesulfonamide,
- 2-{[(2-{4-[(4-Methylphenyl)ethynyl]-2-(tetrahydro-2H-pyran-4-ylmethoxy)phenyl}ethyl)sulfonyl]amino}benzenesulfonamide,
- 2-[({2-[4-(3,3-Dimethylbut-1-yn-1-yl)-2-(tetrahydro-2H-pyran-4-yl-methoxy)phenyl]ethyl}sulfonyl)amino]benzenesulfonamide,
- 2-[({2-[4-chloro-2-(tetrahydro-2H-pyran-4-ylmethoxy)phenyl]ethyl}sulfonyl)amino]-5-(hydroxymethyl)benzenesulfonamide, and
- 2-[({2-[4-fluoro-2-(tetrahydro-2H-pyran-4-ylmethoxy)phenyl]ethyl}sulfonyl)amino]-5-(hydroxymethyl)benzenesulfonamide.

9. A method for treating pain in a patient comprising administering to the patient, a compound of formula (I), or a pharmaceutically acceptable salt thereof, according to claim 1.

10. The method of claim 9, wherein the pain is acute or chronic pain, nociceptive pain or neuropathic pain.

11. A method for treating inflammation in a patient comprising administering to the patient, a compound of formula (I), or a pharmaceutically acceptable salt thereof, according to claim 1.

12. A pharmaceutical composition comprising the compound of formula (I), or a pharmaceutically acceptable salt thereof, according to claim 1 in association with a pharmaceutically acceptable adjuvant, diluent, or carrier.

13. A process for the preparation of a pharmaceutical composition according to claim 12 comprising mixing a compound of formula (I) or a pharmaceutically acceptable salt thereof wherein:
$R^1$ is H or —$CH_2OH$;
$R^2$ is H, halogen, $C_{1-4}$-alkyl, fluoro-$C_{1-4}$-alkyl or —C≡C—$R^3$;
$R^3$ is H, $C_{1-4}$-alkyl, $C_{3-7}$-cycloalkyl or phenyl, wherein phenyl is optionally substituted with one or more substituents independently selected from $C_{1-4}$-alkyl, halogen, $C_{1-4}$-alkoxy and cyano;
X is $CH_2$, CHF, $CF_2$, O, S, SO, $SO_2$, NH or $NR^4$; and
$R^4$ is $C_{1-4}$alkyl;
with a pharmaceutically acceptable adjuvant, diluent or carrier.

14. The pharmaceutical composition of claim 12, further comprising an additional therapeutic agent, or a pharmaceutically acceptable salt thereof.

15. The pharmaceutical composition according to claim 14, wherein the additional therapeutic agent is selected from the group consisting of acetyl cholinesterase inhibitors, anti-inflammatory agents, cognitive enhancing agents, memory enhancing agents and atypical antipsychotic agents.

* * * * *